US012705704B1

(12) United States Patent
Roy

(10) Patent No.: US 12,705,704 B1
(45) Date of Patent: Aug. 11, 2026

(54) SYNTHETIC AUGMENTATION BASED AUTOENCODING NEURAL NETWORK FOR SPECKLE REMOVAL IN INTRACARDIAC ULTRASOUND IMAGING

(71) Applicant: yoR Labs, Inc., Beaverton, OR (US)

(72) Inventor: Anshumali Roy, Beaverton, OR (US)

(73) Assignee: yoR Labs, Inc., Beaverton, OR (US)

( * ) Notice: Subject to any disclaimer, the term of this patent is extended or adjusted under 35 U.S.C. 154(b) by 0 days.

(21) Appl. No.: 19/454,150

(22) Filed: Jan. 20, 2026

(51) Int. Cl.

| | |
|---|---|
| ***G06T 5/60*** | (2024.01) |
| ***A61B 8/00*** | (2006.01) |
| ***A61B 8/08*** | (2006.01) |
| ***G06N 3/0455*** | (2023.01) |
| ***G06N 3/09*** | (2023.01) |
| ***G06T 5/70*** | (2024.01) |

(52) U.S. Cl.
CPC .............. *G06T 5/60* (2024.01); *A61B 8/0883* (2013.01); *A61B 8/5269* (2013.01); *G06N 3/0455* (2023.01); *G06N 3/09* (2023.01); *G06T 5/70* (2024.01); *G06T 2207/10132* (2013.01); *G06T 2207/20032* (2013.01); *G06T 2207/20081* (2013.01); *G06T 2207/20084* (2013.01); *G06T 2207/30048* (2013.01)

(58) Field of Classification Search
CPC ... G06T 5/60; G06T 5/00; G06T 2207/20081; G06T 2207/20084; G06T 5/70; G06T 2207/10132; G06T 2207/10136; G06T 2207/30004; G06T 2207/30048; G06T 2207/20032; A61B 8/5269; A61B 8/0883; G06N 3/0455; G06N 3/045; G06N 3/09; G06N 3/08
See application file for complete search history.

(56) References Cited

U.S. PATENT DOCUMENTS

| | | | | |
|---|---|---|---|---|
| 10,635,943 | B1 * | 4/2020 | Lebel | G06N 3/084 |
| 2022/0138911 | A1 * | 5/2022 | Newey | G06T 5/50 382/100 |

OTHER PUBLICATIONS

Ahmed, Anas Fouad. "Efficient and robust de-speckling filter for ultrasound images based on an attentional auto-encoder." Signal, Image and Video Processing 19.2 (2025): 186. (Year: 2025).*
Bargsten, Lennart, and Alexander Schlaefer. "SpeckleGAN: a generative adversarial network with an adaptive speckle layer to augment limited training data for ultrasound image processing." International journal of computer assisted radiology and surgery 15.9 (2020): 1427-1436. (Year: 2020).*
Karaoğlu, Onur, Hasan Şakir Bilge, and Ihsan Uluer. "Removal of speckle noises from ultrasound images using five different deep learning networks." Engineering Science and Technology, an International Journal 29 (2022): 101030. (Year: 2021).*

(Continued)

*Primary Examiner* — Geoffrey E Summers

(74) *Attorney, Agent, or Firm* — Knobbe, Martens, Olson & Bear, LLP

(57) ABSTRACT

The systems and methods generate synthetic speckle data. The system introduces speckle noise into a clean dataset of images. The system utilizes a machine learning model, such as a model with a convolutional autoencoder architecture, and trains the machine learning model on the synthetic training data. The system uses the trained machine learning model on intracardiac echocardiography images to remove speckle substantially in real-time.

20 Claims, 17 Drawing Sheets

(56) References Cited

OTHER PUBLICATIONS

Lan, Yancheng, and Xuming Zhang. "Real-time ultrasound image despeckling using mixed-attention mechanism based residual UNet." IEEE Access 8 (2020): 195327-195340. (Year: 2020).*

Perreault, Charles, and Marie-Flavie Auclair-Fortier. "Speckle simulation based on B-mode echographic image acquisition model." Fourth Canadian Conference on Computer and Robot Vision (CRV'07). IEEE, 2007. (Year: 2007).*

Sivaanpu, Anparasy, et al. "Speckle noise reduction for medical ultrasound images using hybrid CNN-Transformer network." IEEE Access 12 (2024): 168607-168625. (Year: 2024).*

* cited by examiner

200

SYNTHETIC AUGMENTATION BASED AUTOENCODING NEURAL NETWORK FOR SPECKLE REMOVAL IN INTRACARDIAC ULTRASOUND IMAGING

BACKGROUND

Ultrasound images frequently have a significant amount of speckle. Speckle can refer to the random granular texture that obscures anatomy in ultrasound images and is usually referred to as "noise." Speckle artifacts are caused by a multitude of reasons including random interference of echoes and sub-wavelength scatterers or reflectors, while being also correlated to tissue structure. In some cases, speckle is created by a complex interference of ultrasound echoes made by reflectors spaced closer together than the ultrasound system's resolution limit. In intracardiac echocardiography, speckle is typically a nuisance-obscuring chambers, walls, and valves. Speckle can particularly be a nuisance for interventional cardiologists who are interested in completing procedures and successfully exiting the patient's heart as quickly and safely as possible. There exist image processing filters that can remove or smooth some speckle.

SUMMARY

The systems, methods, and devices described herein each have several aspects, no single one of which is solely responsible for its desirable attributes. Without limiting the scope of this disclosure, several non-limiting features will now be discussed briefly.

In some aspects, the techniques described herein relate to a system including: one or more non-transitory data storage media; and one or more first computer hardware processors in communication with the one or more non-transitory data storage media, wherein the one or more first computer hardware processors are configured to execute first computer-executable instructions to at least: receive a set of tissue images; determine, from the set of tissue images, a set of synthetic speckled tissue images, wherein to determine the set of synthetic speckled tissue images includes: create noise data; modify the noise data with at least a filter that results in speckle filter data; apply, to a first tissue image from the set of tissue images, the speckle filter data as an overlay that results in a first intermediate synthetic speckled tissue image; and transform the first intermediate synthetic speckled tissue image into a first synthetic speckled tissue image in a sector format, wherein the set of synthetic speckled tissue images includes the first synthetic speckled tissue image; determine, from the set of tissue images, a set of images as targets; create a training set including (i) the set of synthetic speckled tissue images and (ii) the set of images as targets; and train a convolutional autoencoder with the training set.

In some aspects, the techniques described herein relate to a system, further including: one or more second computer hardware processors configured to execute second computer-executable instructions to at least: receive a plurality of ultrasound frames during a cardiology procedure; and for each ultrasound frame from the plurality of ultrasound frames, generate, via the convolutional autoencoder, a denoised ultrasound frame, and cause presentation, via a graphical user interface, of the denoised ultrasound frame.

In some aspects, the techniques described herein relate to a system, wherein the set of tissue images includes non-cardiac images.

In some aspects, the techniques described herein relate to a system, wherein to transform the first intermediate synthetic speckled tissue image into the first synthetic speckled tissue image in the sector format includes: edit the first intermediate synthetic speckled tissue image to have a shape including a first straight edge, a second straight edge, and a curved edge.

In some aspects, the techniques described herein relate to a system, wherein to edit the first intermediate synthetic speckled tissue image to have the shape includes: modify pixels in the first intermediate synthetic speckled tissue image without removing any features from the first intermediate synthetic speckled tissue image.

In some aspects, the techniques described herein relate to a system, wherein to edit the first intermediate synthetic speckled tissue image to have the shape includes: crop at least a portion of the first intermediate synthetic speckled tissue image.

In some aspects, the techniques described herein relate to a computer-implemented method including: receiving a set of initial training images; determining, from the set of initial training images, a set of synthetic speckled images, wherein determining the set of synthetic speckled images includes: creating noise data; modifying the noise data with at least a filter that results in speckle filter data; and applying, to a first training image from the set of initial training images, the speckle filter data as an overlay that results in a first synthetic speckled image, wherein the set of synthetic speckled images is determined from the first synthetic speckled image; determining, from the set of initial training images, a set of images as targets; creating a training set including (i) the set of synthetic speckled images and (ii) the set of images as targets; and training a machine learning model with the training set.

In some aspects, the techniques described herein relate to a computer-implemented method, training the machine learning model includes: applying a region-of-interest mask to the training set and implementing a transformer-type attention mechanism that computes attention scores between feature locations, wherein attention in the transformer-type attention mechanism is gated by the region-of-interest mask such a first attention weight outside a masked region is attenuated during training while a second attention weight within the masked region is emphasized, and wherein the transformer-type attention mechanism includes multi-head self-attention or cross-attention between encoder and decoder features.

In some aspects, the techniques described herein relate to a computer-implemented method, further including: receiving a speckle size parameter, wherein modifying the noise data further includes: applying a sector geometric transformation and selecting a kernel size using the speckle size parameter that results in the speckle filter data.

In some aspects, the techniques described herein relate to a computer-implemented method, wherein the speckle size parameter includes at least one of a beam spread or a speckle size growth parameter as a function of depth.

In some aspects, the techniques described herein relate to a computer-implemented method, wherein modifying the noise data further includes: applying a weighted summation to the noise data and filtered data that results in the speckle filter data.

In some aspects, the techniques described herein relate to a computer-implemented method, wherein creating the noise data further includes: determining the noise data from a Rayleigh distribution.

In some aspects, the techniques described herein relate to a computer-implemented method, wherein the filter includes a median filter or a mean filter.

In some aspects, the techniques described herein relate to a system including: one or more non-transitory data storage media; and one or more first computer hardware processors in communication with the one or more non-transitory data storage media, wherein the one or more first computer hardware processors are configured to execute first computer-executable instructions to at least: receive a set of initial training images; determine, from the set of initial training images, a set of synthetic speckled images, wherein to determine the set of synthetic speckled images includes: create noise data; modify the noise data with at least a filter that results in speckle filter data; and apply, to a first training image from the set of initial training images, the speckle filter data as an overlay that results in a first synthetic speckled image, wherein the set of synthetic speckled images is determined from the first synthetic speckled image; determine, from the set of initial training images, a set of images as targets; create a training set including (i) the set of synthetic speckled images and (ii) the set of images as targets; and train a machine learning model with the training set.

In some aspects, the techniques described herein relate to a system, further including: one or more second computer hardware processors configured to execute second computer-executable instructions to at least: receive an ultrasound image; generate, via the machine learning model, a denoised ultrasound image; and cause presentation, via a graphical user interface, of the denoised ultrasound image.

In some aspects, the techniques described herein relate to a system, wherein to determine the set of synthetic speckled images includes: transform the first synthetic speckled image into a sectorized synthetic speckled image, wherein the set of synthetic speckled images includes the sectorized synthetic speckled image.

In some aspects, the techniques described herein relate to a system, wherein the machine learning model corresponds to at least one of a convolutional autoencoder or a U-Net model.

In some aspects, the techniques described herein relate to a system, further including: one or more second computer hardware processors configured to execute second computer-executable instructions to at least: receive a plurality of ultrasound frames during a cardiology procedure; and for each ultrasound frame from the plurality of ultrasound frames, generate, via the machine learning model, a denoised ultrasound frame, and cause presentation, via a graphical user interface, of the denoised ultrasound frame.

In some aspects, the techniques described herein relate to a system, wherein to train the machine learning model includes: apply a region-of-interest mask to the training set and implement a transformer-type attention mechanism that computes attention scores between feature locations, wherein attention in the transformer-type attention mechanism is gated by the region-of-interest mask such a first attention weight outside a masked region is attenuated during training while a second attention weight within the masked region is emphasized, and wherein the transformer-type attention mechanism includes multi-head self-attention or cross-attention between encoder and decoder features.

In some aspects, the techniques described herein relate to a system, wherein to modify the noise data further includes: apply a weighted summation to the noise data and filtered data that results in the speckle filter data.

In some aspects, the techniques described herein relate to a method of training a neural network for image speckle removal, including: collecting a set of digital tissue images; applying one or more transformations to the set of digital tissue images that results in a set of synthetic speckled tissue images, wherein applying the one or more transformations includes: creating noise data; applying, to the noise data, a filter that results in speckle filter data; and applying, to a first digital tissue image, the speckle filter data as an overlay that results in a first synthetic speckled tissue image; determining, from the set of digital tissue images, a set of images as targets; creating a training set including (i) the set of synthetic speckled tissue images and (ii) the set of images as targets; and training the neural network using the training set.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above-and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

These and other features, aspects, and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters can denote corresponding features throughout similar embodiments. The following is a brief description of each of the drawings.

DETAILED DESCRIPTION

Figure 1A:
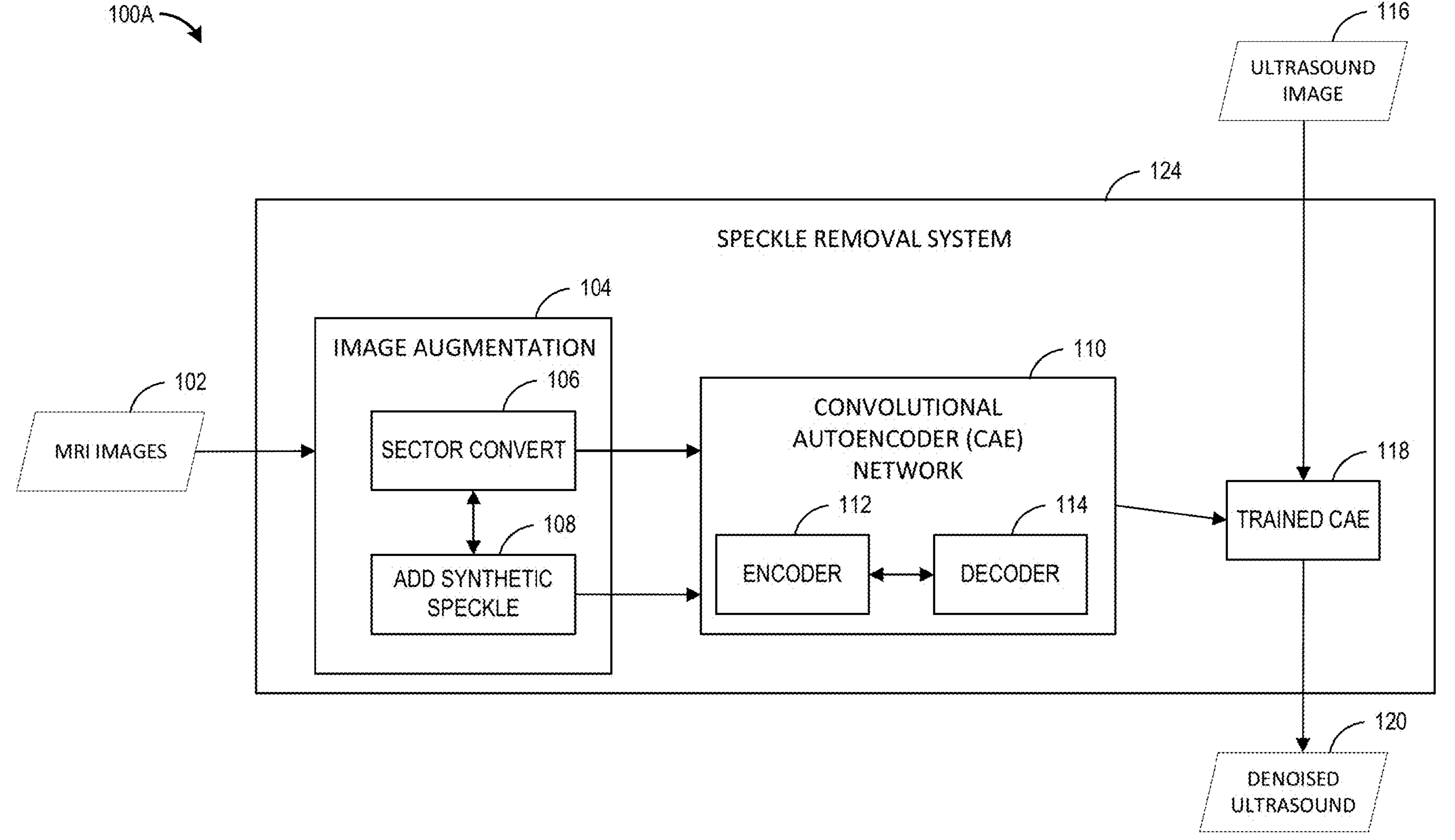
FIG. 1A is a schematic block diagram depicting an example of an environment including a speckle removal system that can remove speckle from intracardiac ultrasound images.

Intracardiac echocardiography (ICE) uses sound waves to produce images of the heart. During intracardiac echocardiography, a narrow catheter with an ultrasound sensor is passed into the heart where images of the heart can be captured. Intracardiac echocardiography has become an integral part of a variety of percutaneous interventional and electrophysiology procedures. As described above, in ICE, speckle is often undesirable. Rather, it would be more advantageous for clinicians to get a clear view of the chambers, valves, and walls in the heart as well. However, often these solid structures are captured in images with speckle. In intracardiac echocardiography images, removing spurious speckle from within chambers can be advantageous. There exists image processing filters, based on mathematical formulas, to remove speckle in images. However, these existing mathematical-formula/image-filter based approaches require relatively large computing resources to operate and/or may not be available during real-time ICE. For example, real-time speckle removal during ICE would assist clinicians; however, such real-time speckle removal with existing techniques are technically challenging, as described herein.

Generally described, aspects of the present disclosure are directed to artificial-intelligence, machine-learning based speckle removal from intracardiac ultrasound images. However, there is a training data problem with respect to training machine learning models to remove speckle from intracardiac ultrasound images. For example, to create training data from an ultrasound image, one existing approach is to have a person manually label parts of the image to identify speckle from non-speckle, which can be a monumental task to do for thousands of images, especially to accurately identify portions of speckle from actual features in the image that should not be removed. Instead, as described herein, synthetic training data can be created to train machine learning models to remove speckle data. In some embodiments, the system generates synthetic speckle data based on a Rayleigh distribution assumption in a rectangular space. The system can utilize a median filter kernel (where the kernel size can be dependent on the final image size) to reshape the distributed Rayleigh noise into speckle in a cartesian space. The system can sectorize a rectangular image based on geometry to reshape the speckle so it is representative of typical speckle size at relative depths. Sectorization can refer to reshaping an image so that it corresponds to the shape of typical ultrasound images. The system can introduce speckle noise as an adder into a clean dataset of images (such as non-cardiac magnetic resonance imaging (MRI) images) that have also been sectorized, via either a sector crop or sector reshape. The system can utilize a machine learning model, such as a model with a convolutional autoencoder architecture of suitable network depth and width with a reasonable number of encoded features, and can train the machine learning model on the synthetic training data (including the clean images and the speckle-generated images). The machine learning model can be trained until a threshold is satisfied, such as loss being sufficiently low and stable. The system can then use the trained machine learning model on ICE images to remove speckle substantially in real-time.

Turning to FIG. 1A, an illustrative environment 100A is shown. The environment 100A can include a speckle removal system 124. The speckle removal system 124 can include an image augmentation process 104, a convolutional autoencoder network 110, and a trained convolutional autoencoder 118. The components of the environment 100A can enable efficient training of the convolutional autoencoder network 110 to remove speckle from intracardiac ultrasound images 116. The image augmentation process 104 can generate synthetic training data. The image augmentation process 104 can receive MRI images 102. As described herein, the MRI images 102 can be non-cardiac images and the convolutional autoencoder network 110 can be trained on the non-cardiac images (such as biological images and/or images of tissue) to remove speckle. For example, the MRI images 102 could be images of the brain. In other cases, the MRI images 102 can be intracardiac images. In yet further embodiments, non-biological images could be utilized, such as pictures of cars.

The image augmentation process 104 can have at least two sub-processes that include a sector convert process 106 and an add synthetic speckle process 108. In some embodiments, synthetic speckle can be added to images first and then sectorized. The add synthetic speckle process 108 adds synthetic speckle to the initial images to result in synthetic speckled images. The speckled images can be converted to sector images by the sector convert process 106. As described herein, a sector shape simulates the shape of an ultrasound image. A sector shape can have two straight edges connected by a curved edge. In some embodiments, the sector convert process 106 sectorizes images by reshaping the images. In other embodiments, the sector convert process 106 sectorizes images by cropping the images. In other embodiments, images can be converted to sectors first and then synthetic speckle can be added to the sector images. As part of the image augmentation process 104, the initial MRI images can be converted to sector images by the sector convert process 106. In some embodiments, the add synthetic speckle process 108 adds synthetic speckle to the converted sector images to result in synthetic speckled images.

The speckle removal system 124 includes the converted sector images in the synthetic training data as the ground truth for denoised images. The speckle removal system 124 includes the synthetic speckled tissue images in the synthetic training data as input to the convolutional autoencoder network 110.

As shown, the convolutional autoencoder network 110 includes an encoder 112 and a decoder 114. The speckle removal system 124 trains the convolutional autoencoder network 110 with the synthetic training data until a threshold is satisfied, such as loss being sufficiently low and/or stable, which results in the trained convolutional autoencoder 118. Based on differences between an original image and output of a denoised image, the speckle removal system 124 can train the convolutional autoencoder network 110, using backpropagation, where the gradient of the loss with respect to the weights is computed and used to update the weights of the convolutional autoencoder network 110.

The speckle removal system 124 can dynamically denoise ultrasound images 116 with the trained convolutional autoencoder 118. The trained convolutional autoencoder 118 can receive the input ultrasound image 116 and outputs a denoised ultrasound image 120. As described herein, the speckle removal system 124 can denoise ultrasound images substantially in real-time during ICE.

Figure 1B:
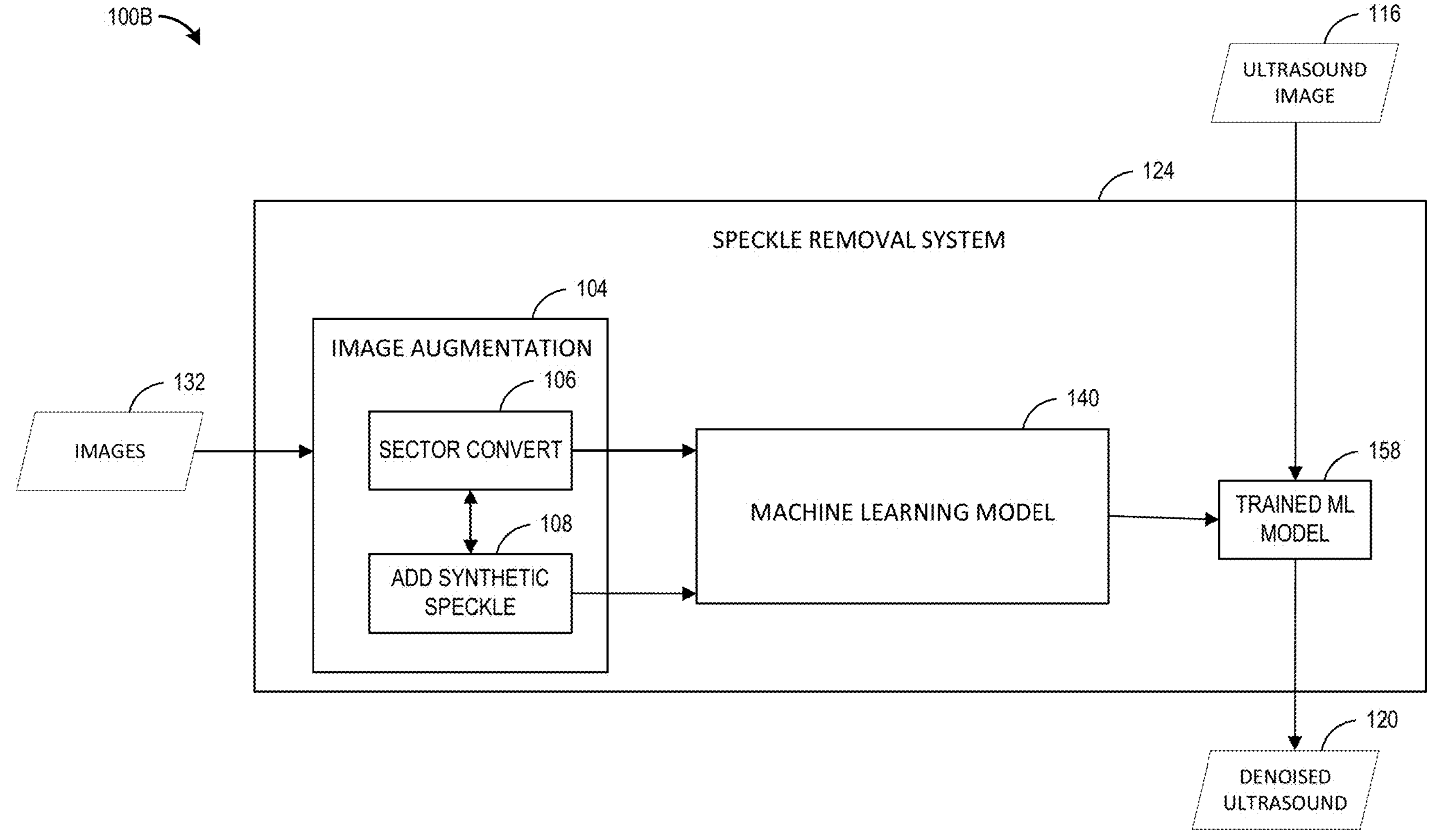
FIG. 1B is a schematic block diagram depicting another example of an environment including another speckle removal system that can remove speckle from intracardiac ultrasound images.

Turning to FIG. 1B, another illustrative environment 100B is shown. The environment 100B can include the speckle removal system 124. The environment 100B and the speckle removal system 124 of FIG. 1B can be similar to the environment 100A and the speckle removal system 124 of FIG. 1A. However, there can be some differences between the speckle removal system 124 of FIG. 1B and the speckle removal system 124 of FIG. 1A. For example, the speckle removal system 124 of FIG. 1B utilizes different and/or additional machine learning model(s) 140 compared to the speckle removal system 124 of FIG. 1A that utilizes a convolutional autoencoder network 110.

As shown, the speckle removal system 124 can include an image augmentation process 104, a machine learning model 140, and a trained machine learning model 158. The components of the environment 100A enable efficient training of the machine learning model 140 to remove speckle from intracardiac ultrasound images 116. The image augmentation process 104 can generate synthetic training data. The image augmentation process 104 can receive images 132. Advantageously, the images 132 can be non-intracardiac images; for example, the images 132 could be MRI images of the brain. In other embodiments, the images 132 can be X-ray images.

The machine learning model 140 can include a convolutional neural network, such as a U-Net model. A U-Net architecture can include a network with a contracting path and an expansive path, which gives it a u-shaped architecture. In some embodiments, the U-Net model can be configured with an encoder-decoder topology and symmetric skip connections that transfer feature information from encoding stages directly to corresponding decoding stages. In a U-Net model, spatial resolution can be reduced step by step through downsampling, but the number of feature channels is increased at each stage to expand representational capacity. Conceptually, as the field of view shrinks by factors of two, the network doubles the filters: for example, progressing from 256 channels to 512, then to 1024 at deeper levels. The design goal is that even though the feature maps become smaller, the model compensates by learning a richer set of features at each reduced resolution. Also, as mentioned, a U-Net model can use skip (also known as short-circuit) connections to pass early features to later decoder stages. Benefits of U-Net utilization can include retaining fine detail; and, in some cases, downsides can include propagating input noise to the output and more complex, harder training. Additional details regarding U-Net models are provided herein, such as with respect to FIG. 4C.

In some embodiments, the machine learning model 140 can incorporate transformer-type attention that enables each spatial location to weight and aggregate information from all other locations based on learned importance scores. The attention can operate as self-attention within a feature map or as cross-attention that aligns decoder features with encoder features or auxiliary guidance signals, such as user-identified regions of interest or anatomical priors. The mechanism can function in a purely data-driven manner or be partially guided, improving focus on salient structures while retaining the ability to automatically detect informative regions. However, attention may increase the risk of propagating noisy detail to the output because speckle-like artifacts can be present and correlated across many pixels and neighborhoods. Given the variable and context-dependent nature of ultrasound speckle, controls such as confidence-weighted gating, sparsity or entropy regularization of attention weights, and/or depth-aware biasing can be employed to mitigate noise amplification while preserving anatomical detail.

The image augmentation process 104 can have at least two sub-processes that include the sector convert process 106 and the add synthetic speckle process 108. As described herein, the sector convert process 106 performs sectorization. As described herein, the add synthetic speckle process 108 adds synthetic speckle to the images to result in synthetic speckled images. The speckle removal system 124 includes the synthetic speckled images in the synthetic training data as input to the machine learning model 140.

The speckle removal system 124 trains the machine learning model 140 with the synthetic training data until a threshold is satisfied, such as loss being sufficiently low and/or stable, which results in the trained machine learning model 158. Based on differences between an original image and output of a denoised image, the speckle removal system 124 can train the machine learning model 140, using backpropagation, where the gradient of the loss with respect to the weights is computed and used to update the weights of the machine learning model. The speckle removal system 124 can dynamically denoise ultrasound images 116 with the trained machine learning model 158. The trained machine learning model 158 receives the input ultrasound image 116 and outputs a denoised ultrasound image 120. As described herein, the speckle removal system 124 can denoise ultrasound images substantially in real-time during ICE.

In some embodiments, advantages of the approaches described with respect to the speckle removal system 124 of FIGS. 1A and 1B include that the training process can start with images that do not have any speckle in them, such as speckle that is not visible to a human observer. For example, the MRI images 102 of FIG. 1A have the characteristic of having well delineated features and little to no speckle. In some cases, despite some X-ray images having a translucent characteristic, X-ray images can be better than ultrasound with respect to speckle; some images 132 of FIG. 1B can be X-ray images. By starting with images without speckle or a relatively small amount of speckle, the problem of methodically of going through ultrasound images and marking out areas where there is speckle and other areas that do not have speckle can be avoided as a technically challenging task.

Speckle removal or despeckling is an image processing computer technology for removing speckle in digital images. As described herein, speckle can degrade image quality and/or can hinder image interpretation. Prior methods for speckle removal include image processing filters, which can be based on mathematical formulas, to remove speckle in images. Moreover, as described herein, these existing mathematical-formula/image-filter based approaches require relatively large computing resources to operate. In some embodiments, this issue is addressed via the training of a machine learning model and usage of a trained machine learning model configured to remove speckle, which can be operated with fewer computing resources than the prior methods. Accordingly, the systems and methods described herein can improve existing image processing computer technology.

Moreover, training machine learning models for image processing tasks can be technically challenging. For example, to create training data from ultrasound images, prior methods would use manual labelling of parts of the image (e.g., is speckle, or is not speckle), which can be a monumental task to do for thousands of images. In some embodiments, synthetic training data can be created to train machine learning models to avoid the training data creation problem. Accordingly, some approaches described herein begin with images that do not have speckle in them, which address a technical data problem in machine learning training. With improved training data, machine learning models for speckle removal can be trained efficiently. Accordingly, the systems and methods described herein can improve existing machine learning training technology.

Figure 2:
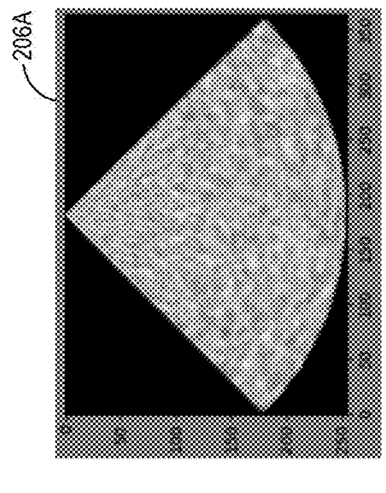
FIG. 2 is a diagram depicting example noise data.
Figure 2:
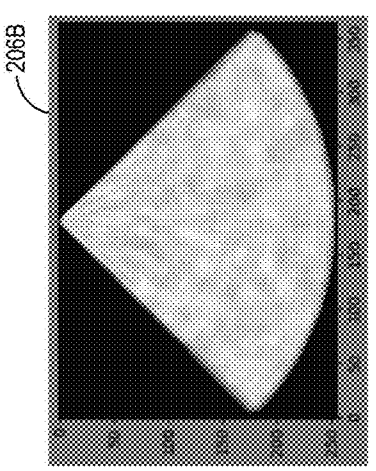
Figure 2:
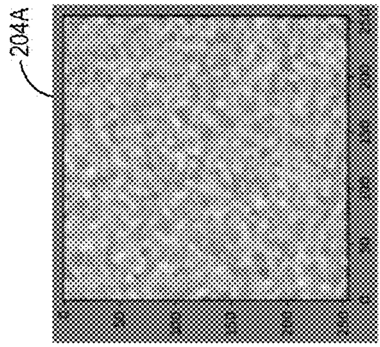
Figure 2:
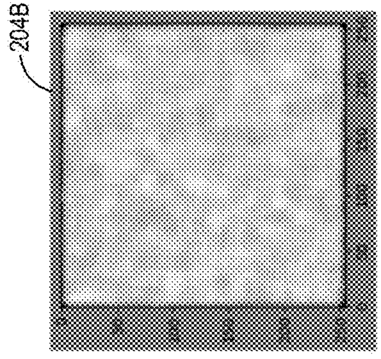
Figure 2:
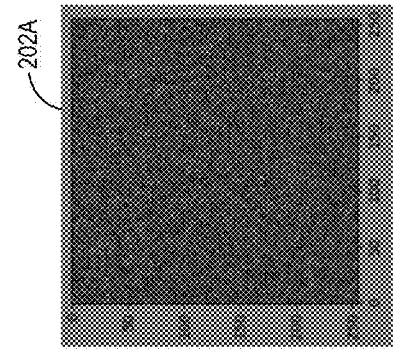
Figure 2:
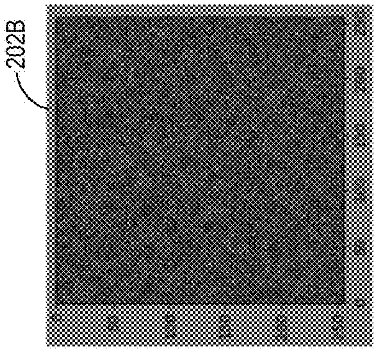

Turning to FIG. 2, an environment 200 is shown with illustrative noise data. As described herein, a speckle noise creation model or process can be advantageously used to create the example noise data shown in FIG. 2. The environment 200 can include first noise data 202A, first filtered noise data 204A, and first sector noise data 206A. The first noise data 202A, first filtered noise data 204A, and first sector noise data 206A can be used to create a wide diversity of speckle data for ultrasound images of particular dimensions (such as 256×256, 1024×1024, 1400×1400, 1400×1000, or 2048×2048). The dimensions of interest (such as 256×256, 1024×1024, 1400×1400, 1400×1000, or 2048×2048) can be selected based on the available computing resources of the host computing device that will utilize the noise data. Larger dimensions of noise data can require greater computing resources.

The first noise data 202A can be based on a Rayleigh distribution. The Rayleigh distribution is a probability distribution used to describe the magnitude of a random variable with phase and amplitude. A random number generator, such as a Rayleigh noise generator function, can be utilized to generate the first noise data 202A. The Rayleigh probability density function is given in Table 1 below, where σ is the scale parameter of the distribution.

TABLE 1

$$f(x) = \begin{cases} \frac{x}{\sigma^2} e^{\left(-\frac{x^2}{2\sigma^2}\right)}, & x \geq 0 \\ 0, & x < 0 \end{cases}$$

A filter can be applied to the first noise data 202A that results in the first filtered noise data 204A. The filter can be a median filter or a mean filter. The filter size can be configured to be roughly proportional to the resolution of the images. In some embodiments, a median filter processes each pixel in an image in turn and looks at its nearby neighbor pixels. Instead of replacing the pixel value with the mean of neighboring pixel values, it replaces it with the median of those values. The median can be calculated by first sorting all the pixel values from the surrounding neighborhood (also known as a kernel) into numerical order and then replacing the pixel being considered with the middle pixel value. In the example with the first filtered noise data 204A, a first kernel can be 7×7 pixels. As shown, the first filtered noise data 204A is transformed into the first sector noise data 206A.

The environment 200 can further include second noise data 202B, second filtered noise data 204B, and second sector noise data 206B, which can be similar to the first noise data 202A, the first filtered noise data 204A, and the first sector noise data 206A, respectively. The second noise data 202B can also be based on a Rayleigh distribution. A filter can also be applied to the second noise data 202B that results in the second filtered noise data 204B. However, the second kernel for the filter applied to the second noise data 202B can be different from the first kernel. For example, the second kernel can be 15×15 pixels. As shown, the second filtered noise data 204B is transformed into the second sector noise data 206B. As shown, the first sector noise data 206A and second sector noise data 206B can have two straight edges and a curved edge. Also, as shown, the two straight edges of the first sector noise data 206A and second sector noise data 206B can form an angle, here 90 degrees. In some embodiments, sector noise data can be created of with different angles or a set of angles, such as between 20 and 90 degrees (20°, 21°, 22°, etc.; 20°, 25°, 30°, etc.; or 20°, 30°, 40°, etc.).

The first sector noise data 206A and second sector noise data 206B can advantageously simulate the physical phenomenon of speckle that appears in ultrasound images. For example, in both the first sector noise data 206A and the second sector noise data 206B, as the shape widens (in the direction of the value "250" on the Y axis), the speckle gets more stretched out in the horizontal direction. For filtering purposes, some kernel sizes (such as 7×7 or 15×15) work better than others. For example, based on the kernel size, some filtered noise data that are converted into sector noise data approximate actual speckle better than others. As described herein, an iterative loop and a metric can be applied during speckle generation with different kernel sizes to identify speckle noise data that satisfies a threshold.

In the environment 200 of FIG. 2, in some embodiments, the synthetic speckle generation process can include using multiple sector options based on specified (such as user-specified) parameters for beam spread and/or speckle size growth parameter as a function of depth. For example, a user, such as an ultrasound physicist, can input a speckle size parameter that defines axial and lateral speckle extension per unit of distance (such as centimeter) and per scan line, together with sector angle and depth metadata. The speckle removal system 124 can apply geometric transformations to the speckle field in sector format so that speckle elongation widens with depth consistent with the supplied function, while preserving the overall sector shape and the mapping between the rectangular source image and the sectorized output. To avoid over-specialization to any single frequency or probe configuration, the speckle removal system 124 can generate training sets across a range of inputs (such as user inputs) and sector angles, enabling the machine learning model 140 to learn robust despeckling behavior over diverse operating conditions. The baseline geometric transformation can produce a broad variety of speckle characteristics in a single image. The input-driven sector options described herein can be an optional refinement that can be enabled for greater specificity or disabled to maintain generalization.

Figure 3A:
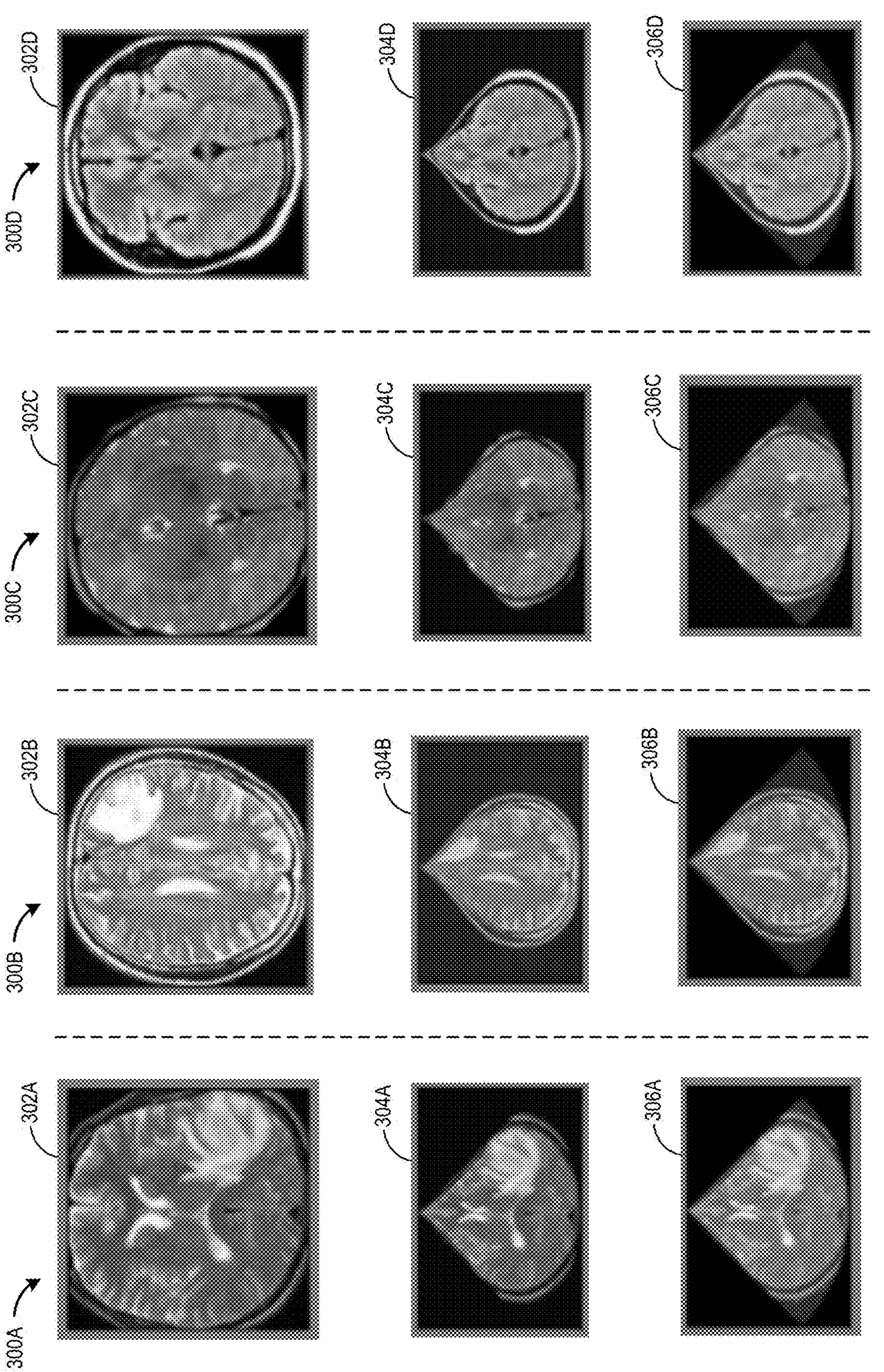
FIGS. 3A, 3B, and 3C depict example source images and synthetic training data images.
Figure 3B:
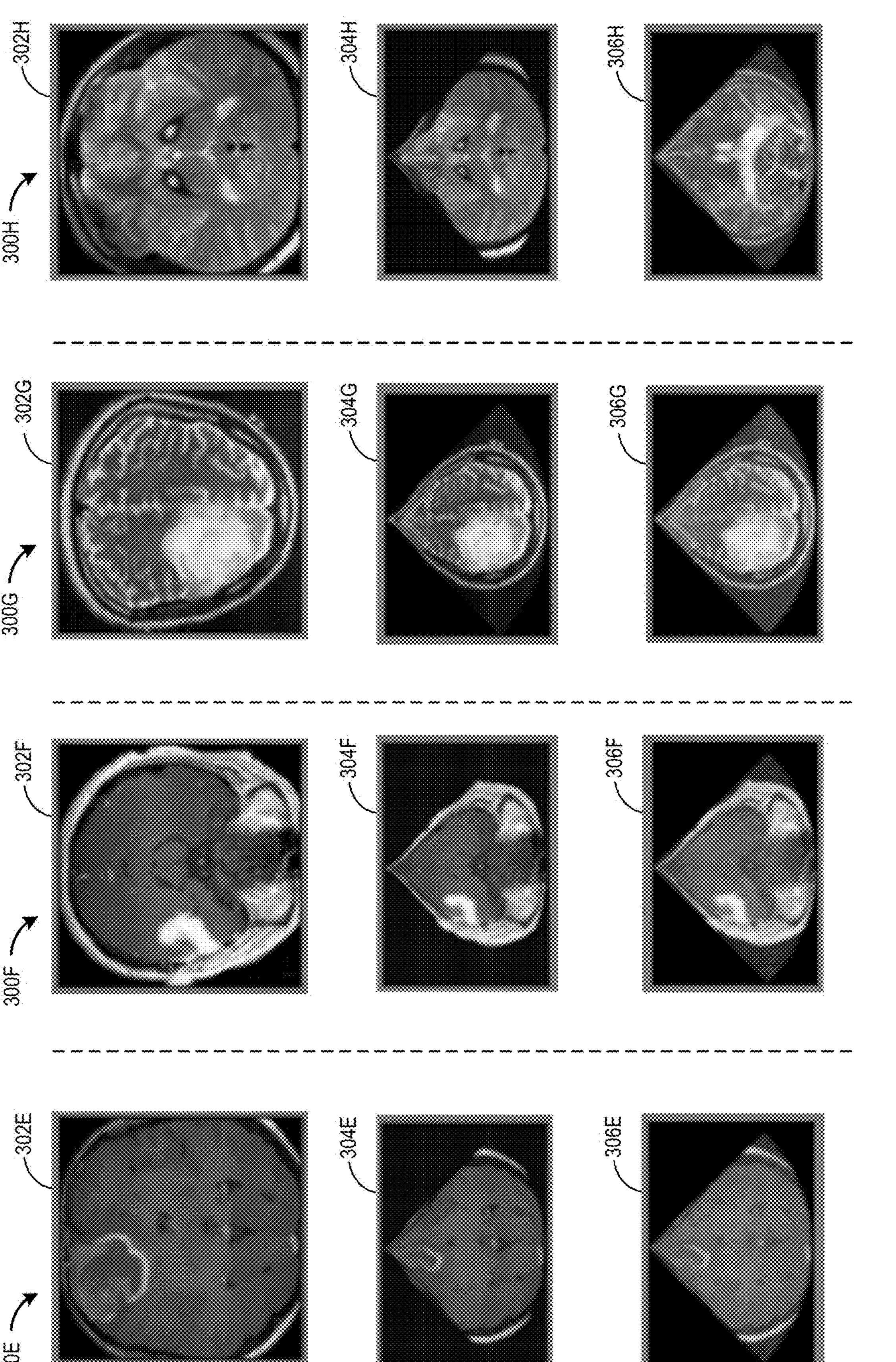
Figure 3C:
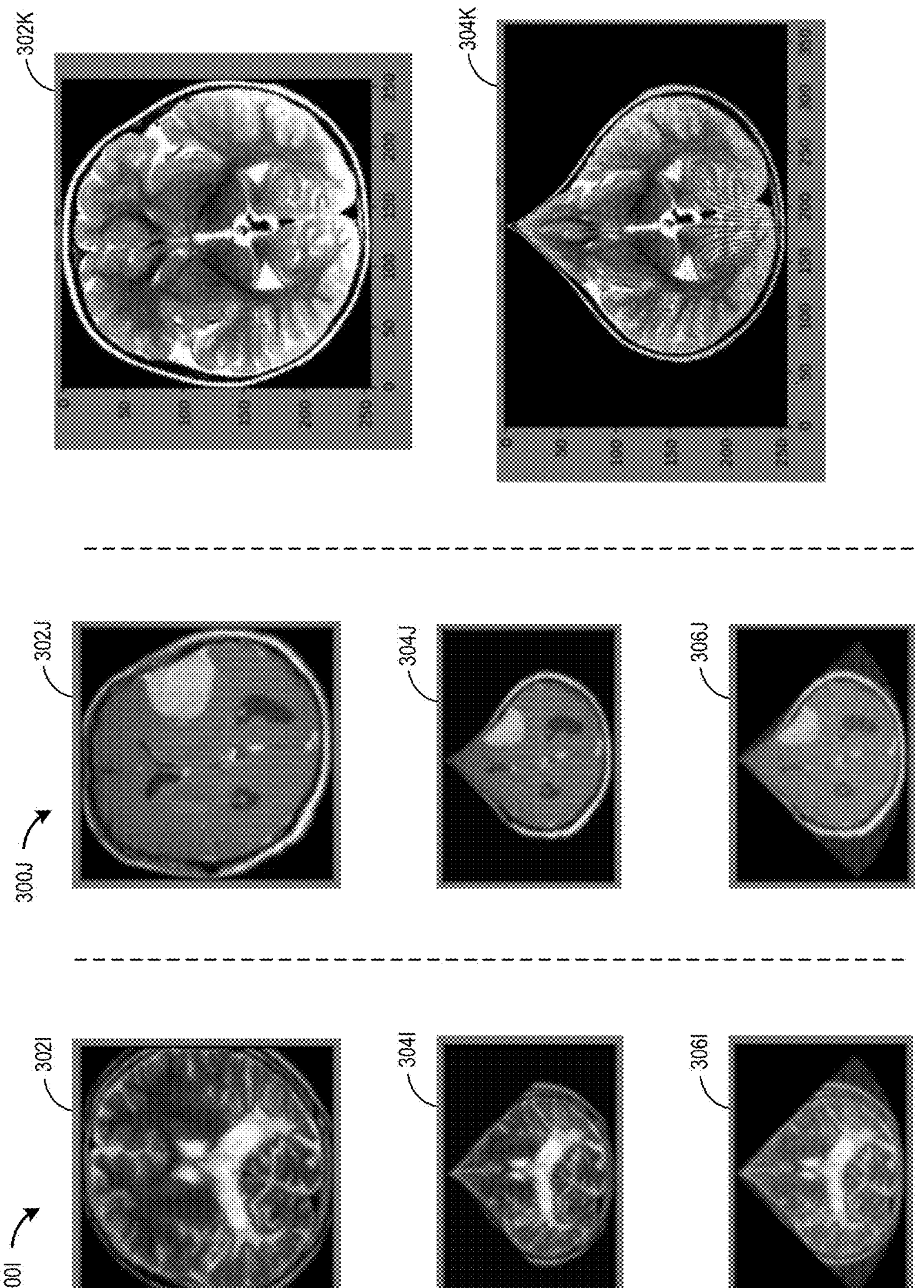

FIGS. 3A, 3B, and 3C depict example source images and synthetic training data images. As shown in FIGS. 3A, 3B, and 3C, the source images 302A, 302B, 302C, 302D, 302E, 302F, 302G, 302H, 302I, and 302J can be used as the basis for a synthetic training set. Each of the source images 302A, 302B, 302C, 302D, 302E, 302F, 302G, 302H, 302I, and 302J are brain MRI images. As shown, each of the source images 302A, 302B, 302C, 302D, 302E, 302F, 302G, 302H, 302I, and 302J can be converted into sector format images 304A, 304B, 304C, 304D, 304E, 304F, 304G, 304H, 304I, and 304J, respectively. As described herein, a speckle filter (such as an overlay) can be applied to the sector format images 304A, 304B, 304C, 304D, 304E, 304F, 304G, 304H, 304I, and 304J that results in the synthetic speckled tissue images 306A, 306B, 306C, 306D, 306E, 306F, 306G, 306H, 306I, and 306J, respectively.

In FIGS. 3A, 3B, and 3C, the source images and synthetic training data images are grouped into sets 300A, 300B, 300C, 300D, 300E, 300F, 300G, 300H, 300I, and 300J. For example, in the first set 300A, the first source image 302A is converted into the first sector format image 304A and the first sector format image 304A is transformed into the first synthetic speckled tissue image 306A; in the second set 300B, the second source image 302B is converted into the second sector format image 304B and the second sector format image 304B is transformed into the second synthetic speckled tissue image 306B; and so forth.

In FIG. 3C, another source image 302K is depicted. As shown, the additional source image 302K can have a particular dimension (such as 256×256). The additional source image 302K (which can have a rectangular or squarish shape) can be sectorized, via reshaping, into the additional sector format image 304K. As shown, the additional source image 302K can be reshaped into a wider dimension in the additional sector format image 304K (such as 256×378). In some embodiments, vertical bars in the additional source image 302K can be remapped into the additional sector format image 304K. For example, pixels in the first row (such as at the value 0 on the Y axis) of the additional source image 302K can be converted to a single pixel in the additional sector format image 304K. Geometric interpolation can also be applied in converting the additional source image 302K into the additional sector format image 304K. Due to the reshaping sectorization approach utilized to create the additional sector format image 304K, every feature in the additional source image 302K can be present in the additional sector format image 304K. In other embodiments, a different sectorization can be utilized whereby a source image is cropped into a sector shape. However, such a cropping sectorization approach may crop out some features in the source image, but such sector images can still be utilized to train a machine learning model to remove speckle with sufficient accuracy, as described herein.

In some embodiments, the speckle removal system 124 can overlay sector-converted speckle with additional Rayleigh-distribution-based noise components in a selectable (such as user-selectable) manner to produce more versatile and/or realistic synthetic speckle and to control which visual artifacts are minimized. In some embodiments, the speckle removal system 124 can use a weighted summation where sectorized speckle (such as the first sector noise data 206A of FIG. 2) is combined with Rayleigh noise (such as the first noise data 202A of FIG. 2) and a filtered Rayleigh component (such as the first filtered noise data 204A of FIG. 2) before being added to a sectorized source image (such as the sector format image 304A of FIG. 3A) times some factor. For example, 0.80×the sectorized speckle 206A+0.15×Rayleigh noise 202A+0.05×filtered Rayleigh component 204A, scaled by a factor and then summed with the original image. The weighted sum combination can capture dot-like or cloud-like scatterers observed in ultrasounds, including blood flow and sub-wavelength reflectors that do not manifest as classic speckle, and can themselves be sectorized by applying a sector stencil to the Rayleigh field prior to overlay. Users can adjust the relative weights and scaling to match the perceived noise regime of a given modality, and the approach supports source images from MRI, computed tomography, or cleaner ultrasound modalities (such as transesophageal echocardiogram), thereby helping ICE denoising training close the visual clarity gap while maintaining anatomically faithful structure in the synthetic data.

Figure 4A:
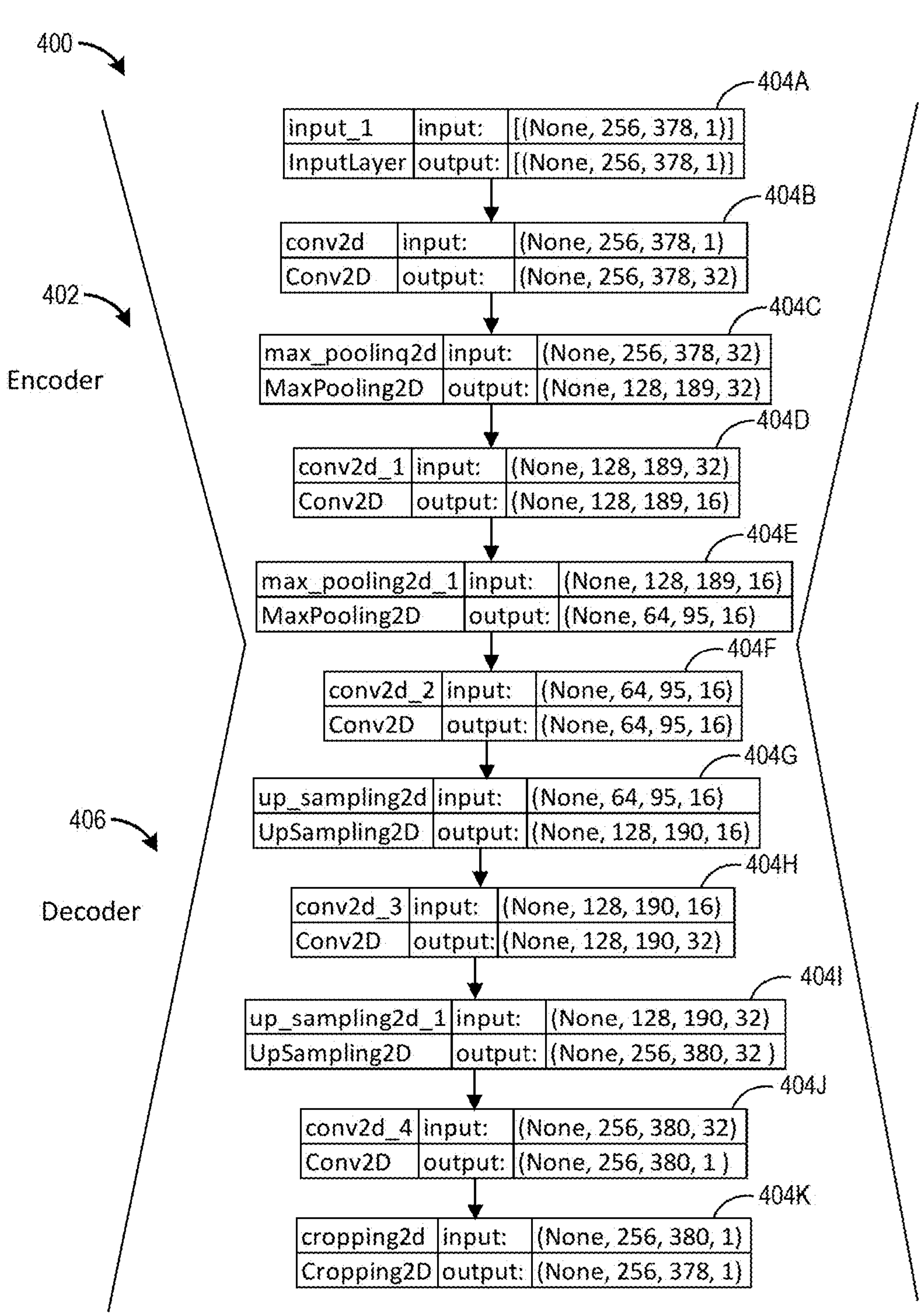
FIGS. 4A, 4B, and 4C are schematic diagrams depicting example machine learning models and layers of the example machine learning models.

FIG. 4A depicts layers of an example convolutional autoencoder 400. As shown, the convolutional autoencoder 400 includes an encoder 402 and a decoder 406. The convolutional autoencoder 400 can be a type of artificial neural network that is configured to extract features and generate a representation of data through convolutional layers. The convolutional autoencoder 400 can learn two functions: an encoding function that transforms the input data, and a decoding function that creates data from the encoded representation. The convolutional autoencoder 400 can learn an encoding for a set of data.

The convolutional autoencoder 400 can include an input layer 404A, hidden layers 404B, 404C, 404D, 404E, 404F, 404G, 404H, 404I, and 404J, and an output layer 404K. As shown, some of the hidden layers 404B, 404C, 404D, 404E, 404F, 404G, 404H, 404I, and 404J are configured to perform convolutions. A convolution can refer to a mathematical operation that combines two sets of data, such as a kernel and an input image, to produce a new feature map. As shown, each of the layers 404A, 404B, 404C, 404D, 404E, 404F, 404G, 404H, 404I, 404J, and 404K have inputs and outputs. Each input and output can include a height, width, and a channel. The convolutional autoencoder 400 can have thousands of parameters, such as parameters describing model weights.

The initial convolutional and pooling layers of the convolutional autoencoder 400 can progressively reduce the spatial dimensions (width and height) of the input and intermediate feature maps, a process which can be referred to as encoding or downsampling. As shown in FIG. 4A, the example convolutional autoencoder 400 can start with an image of a first size (here 256×378 at the first layer 404A) and minimize the image down to a second size and multiple channels (such as, 64×95 with 16 channels at the sixth layer 404F). As described herein, convolutional layers can perform convolutions that include mathematical operations to combines two sets of data. In the encoder portion 402 of the convolutional autoencoder 400, the second layer 404B and the fourth layer 404D can be or correspond to convolutional layers. Some of the layers in the convolutional autoencoder 400 can be max pooling layers. Max pooling can refer to a downsampling technique used in the convolutional autoencoder 400 to reduce the spatial dimensions of an input volume. In the encoder portion 402 of the convolutional autoencoder 400, the third layer 404C and the fifth layer 404E can be or correspond to max pooling layers. In some embodiments, max pooling may not be used. For example, instead of max pooling, the data can be strided in steps of two. However, depending on the case, max pooling can work better than striding in steps of two.

As described herein, it can be desirable for the convolutional autoencoder 400 to reverse the process by restoring the spatial dimensions of the feature maps while reducing the number of channels and/or features. This process can be referred to as upsampling, decoding, unpooling, or upscaling. In the decoder portion 406 of the convolutional autoencoder 400, the sixth layer 404F, the eighth layer 404H, and the tenth layer 404J can be or correspond to convolutional layers. Some of the layers in the convolutional autoencoder 400 can be upsampling layers. The seventh layer 404G and the ninth layer 404I can be or correspond to upsampling layers. The upsampling layers, such as the seventh layer 404G and the ninth layer 404I, can perform interpolation methods, such as, but not limited to, nearest neighbor, max unpooling, bilinear interpolation, bicubic interpolation, and/or Lanczos interpolation. A layer can reduce the width or height of an image, such as by performing cropping of an image. A layer in the decoder portion 406 of the convolutional autoencoder 400, the eleventh or last layer 404K can be or correspond to a cropping layer that crops an image.

Figure 4B:
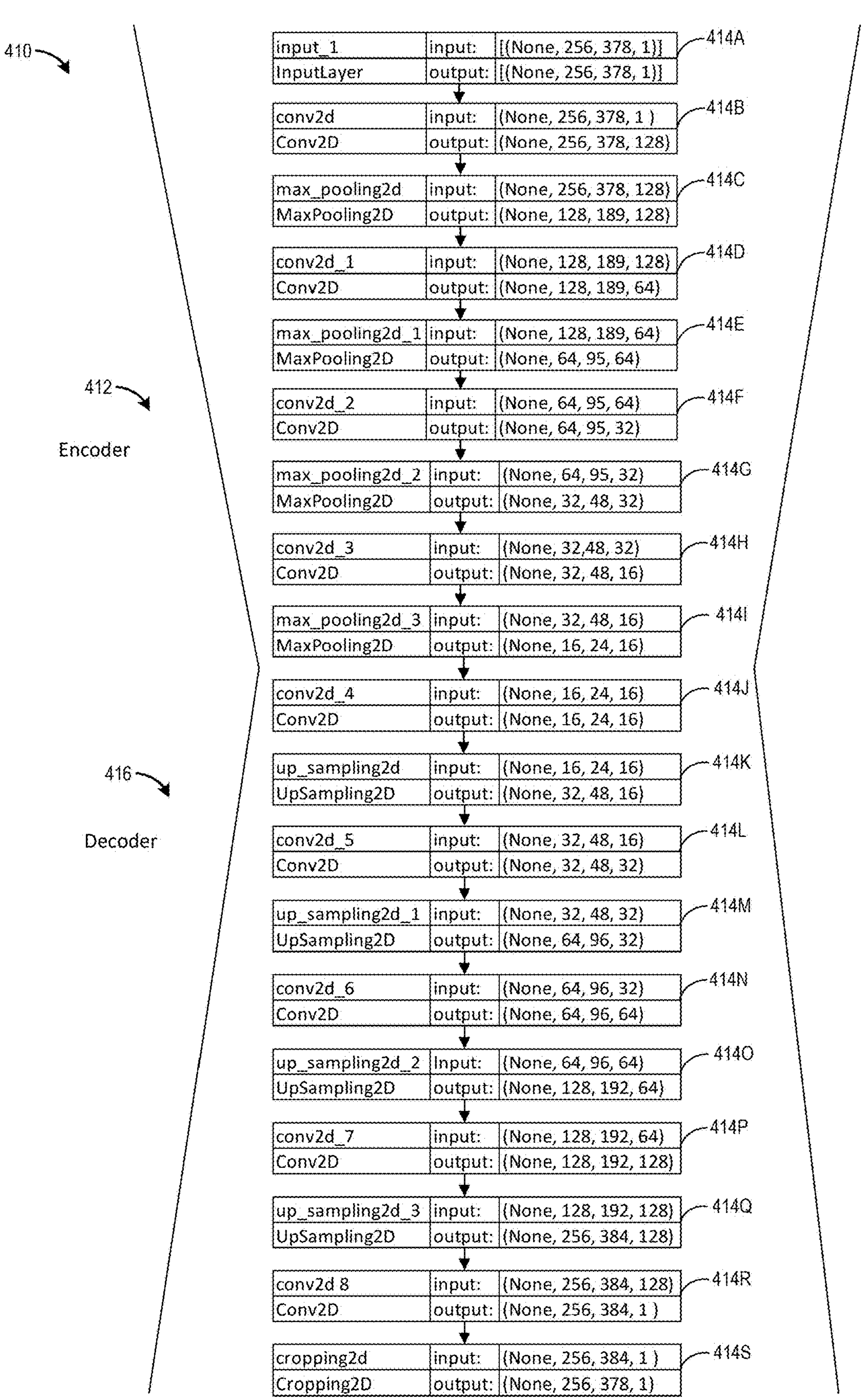

FIG. 4B depicts layers of another example convolutional autoencoder 410. The example convolutional autoencoder 410 of FIG. 4B can be similar to the example convolutional autoencoder 400 of FIG. 4A. For example, the convolutional autoencoder 410 of FIG. 4B includes an encoder 412 and a decoder 416. However, as shown, the convolutional autoencoder 410 of FIG. 4B can have more layers 414A, 414B, 414C, 414D, 414E, 414F, 414G, 414H, 414I, 414J, 414K, 414L, 414M, 414N, 414O, 414P, 414Q, 414R, and 414S than the layers 404A, 404B, 404C, 404D, 404E, 404F, 404G, 404H, 404I, 404J, and 404K of the convolutional autoencoder 400 of FIG. 4A. In addition to having more layers, the convolutional autoencoder 410 of FIG. 4B can have more parameters (such as hundreds of thousands of parameters) than the convolutional autoencoder 400 of FIG. 4A.

The encoder portion 412 of the convolutional autoencoder 410 of FIG. 4B can be similar to the encoder portion 402 of the convolutional autoencoder 400 of FIG. 4A. For example, the encoder portion 412 of the convolutional autoencoder 410 of FIG. 4B can progressively reduce the spatial dimensions (width and height) of the input and intermediate feature maps with convolution and pooling layers. The decoder portion 416 of the convolutional autoencoder 410 of FIG. 4B can be similar to the decoder portion 406 of the convolutional autoencoder 400 of FIG. 4A. For example, the decoder portion 416 of the convolutional autoencoder 410 of FIG. 4B can restore the spatial dimensions of the feature maps while reducing the number of channels and/or features. As shown, the decoder portion 416 of the convolutional autoencoder 410 of FIG. 4B can include convolutional, upsampling, and cropping layers.

Relative to the example convolutional autoencoder 410 of FIG. 4B, the example convolutional autoencoder 400 of FIG. 4A can be referred to as a "shallow" or "skinny" model since the convolutional autoencoder 400 of FIG. 4A can have fewer layers, fewer parameters, and/or be smaller in size than the convolutional autoencoder 410 of FIG. 4B. In some cases, such as in the use case of a deployable model to perform substantially in real-time speckle removal during live ultrasound imaging, a shallow machine learning model can be advantageous to a larger model for deployability and/or usability purposes. It can be technically more efficient to deploy a machine learning model with a smaller footprint and/or utilize a machine learning model with a smaller footprint for substantially in real-time speckle removal during live ultrasound imaging.

Figure 4C:
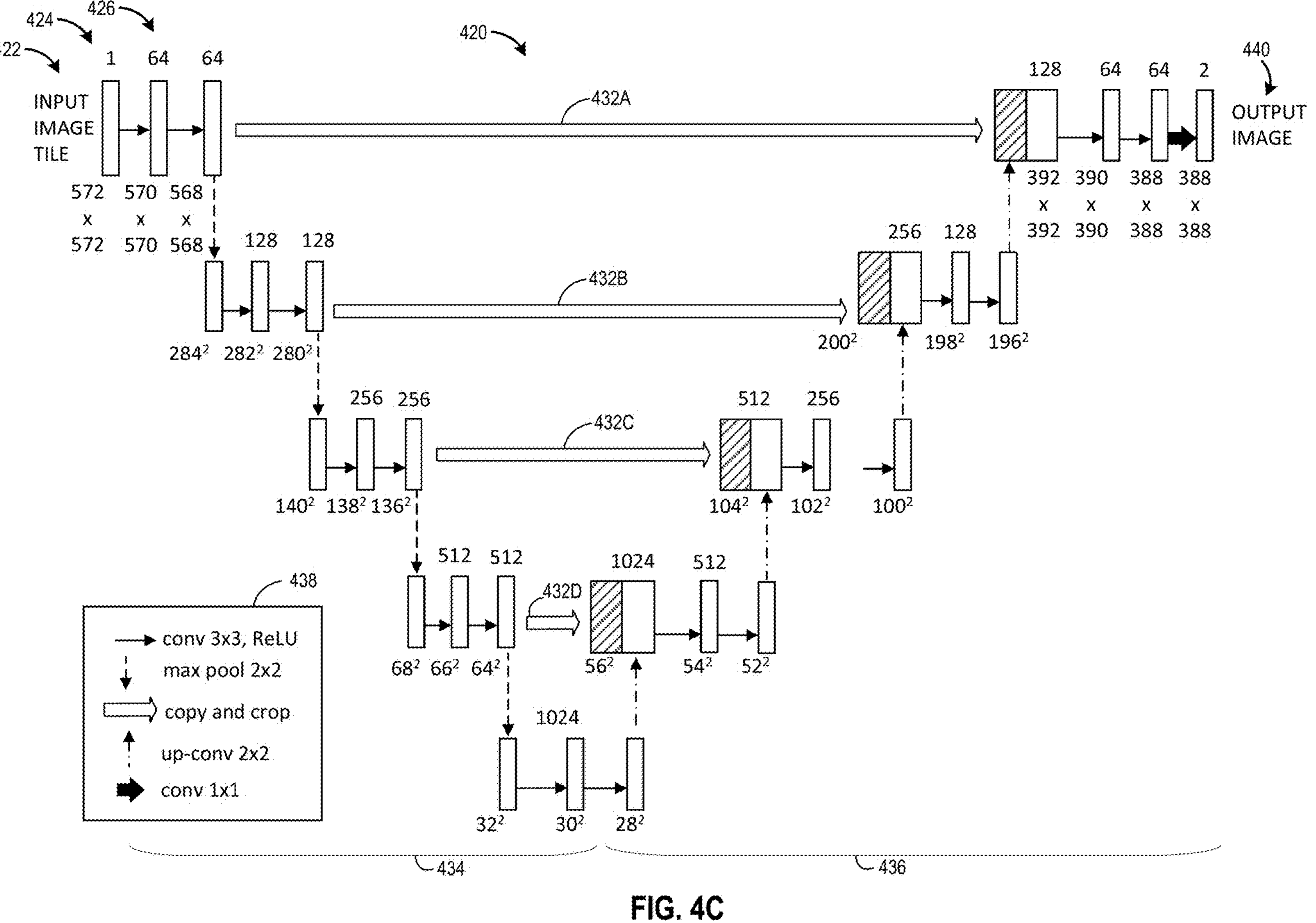

FIG. 4C depicts an example machine learning model (a U-Net model) 420 with a U-Net architecture. As shown, the architecture of the U-Net model 420 can include a network with a contracting path 434 and an expansive path 436, which gives it a u-shaped architecture. The U-Net model can receive an input image tile 422 and generate an output image 440. In the diagram of FIG. 4C, each block can represent a multi-channel feature map. For each feature map, the number of channels is denoted on the top of the box and the x-y size is provided below the box. For example, the first feature map 424 can have one channel and an x-y size of 572×572 pixels and the second feature map 426 can have sixty-four channels and an x-y size of 570×570 pixels. The parameters of the U-Net model 420 depicted in FIG. 4C can be illustrative and, depending on the embodiment, different parameters can be used. In some embodiments, the parameter count of a U-Net model can be relatively flat throughout, allowing for enriched feature finding, and/or the skip connections can allow for better relationship feature anchoring vis-a-vis incoming images.

In a U-Net model, a skip connection can be a direct pathway that transfers feature maps from an encoder stage to the corresponding decoder stage at the same spatial scale. The skip connections in a U-Net model can anchor fine-grained, spatially precise features from early encoder layers to the corresponding decoder stages where resolution is being restored. In other words, the skip connections can help the decoder retain and align fine, spatially precise features learned early in the encoder with the higher-level, context-rich features learned deeper in the network. By concatenating these shallow, high-frequency feature maps with the upsampled, context-rich decoder maps, the U-Net model can preserve local detail (edges, boundaries, and/or small structures) while integrating broader semantic context from deeper layers. This direct pathway can reduce information loss from downsampling, improve gradient flow for training stability, and/or enable the decoder to reference original spatial cues when reconstructing the output. As a result, anatomical structures can be better localized and/or the relationships between nearby features can be maintained, yielding more accurate, detail-aware predictions. In a U-Net model, a skip connection can be implemented by copying the encoder feature map and cropping it to match the spatial dimensions of the corresponding decoder feature map, then concatenating them, which can be referred to as copy-and-crop. This copy-and-crop step can align sizes when valid (unpadded) convolutions shrink encoder maps, enabling the skip connection to fuse higher-resolution detail with upsampled decoder features.

In the legend 438 of FIG. 4C, the different types of arrows correspond to different operations in the U-Net model 420. For example, an input image tile is provided to a contracting path that performs successive pairs of 3×3 convolutions with Rectified Linear Unit (ReLU) activations, followed by 2×2 max-pooling for downsampling at each level. A 3×3 convolution can refer a neural network operation that applies a 3-by-3 kernel (filter) to an input feature map to produce an output feature map. A ReLU activation can refer to a nonlinear function used in neural networks that outputs the input if it is positive and zero otherwise. A 2×2 max-pooling can refer to a downsampling operation that partitions an input feature map into non-overlapping 2-by-2 windows and replaces each window with its maximum value. As spatial resolution decreases, the number of feature channels can increase to expand representational capacity; for example, the feature depth can progress through stages such as 64, 128, 256, 512, and 1024 channels at the bottleneck. The convolution blocks can use valid convolutions, so the feature maps can slightly shrink at each convolution; therefore, before concatenation in the expansive path 436, the corresponding encoder feature maps can be copied and cropped to match the decoder's spatial dimensions. In the model 420, the boxes with diagonal patterns can represent copied feature maps.

During the expansive path 436, resolution can be restored using 2×2 up-convolutions (transposed convolutions) at each level, which can halve the number of feature channels. After each up-convolution, the decoder can concatenate the upsampled features with the size-matched encoder features via the copy-and-crop skip connection 432A, 432B, 432C, or 432D and can apply two 3×3 convolutions with ReLU to fuse higher-resolution spatial detail with contextual information propagated from deeper layers. The copy-and-crop skip connections 432A, 432B, 432C can correspond to operations in which a feature map from an encoder stage is duplicated and spatially cropped to match the dimensions of the corresponding upsampled decoder feature map, after which the cropped encoder feature map can be concatenated with the decoder feature map. This process can continue until the output reaches the input or near-input resolution, at which point a final 1×1 convolution maps the features to the desired number of output channels to form the output image 440. The illustrated dimensions show an example flow in which an input image tile 422 of 572×572 pixels can be progressively downsampled and then upsampled back to produce the output image 440 of approximately 388×388 pixels with two output channels. As described herein, in some U-Net model embodiments, different pixel x-y sizes can be used for the input image and/or the output image.

Figure 5A:
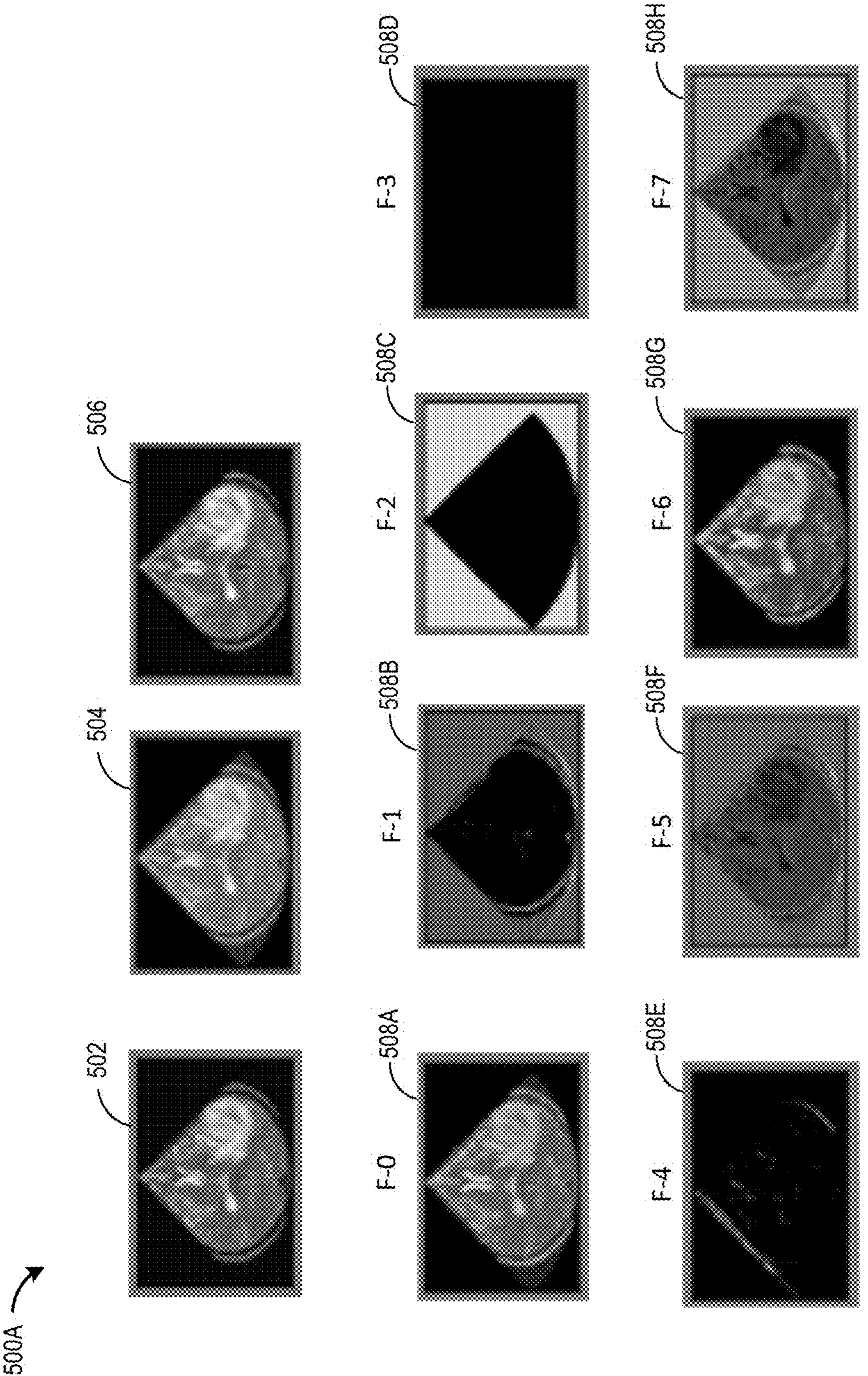
FIGS. 5A and 5B depict examples of an original image, a synthetic speckled image, a denoised image, and the feature maps of a machine learning model, such as a convolutional autoencoder, after machine learning training.
Figure 5B:
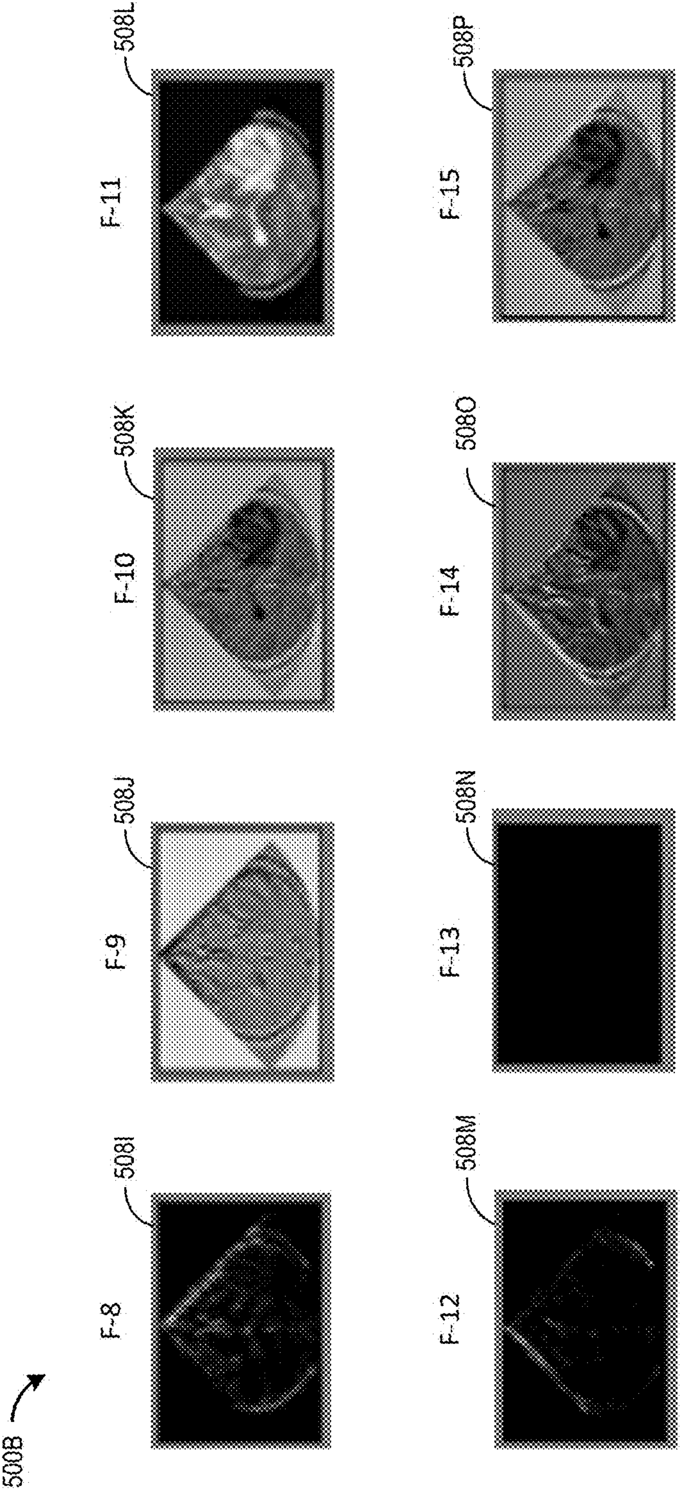

FIGS. 5A and 5B depict examples of an original image, a synthetic speckled image, a denoised image, and feature maps following machine learning training. In FIGS. 5A and 5B, the example original images, synthetic speckled images, and denoised images can be utilized to validate a trained machine learning model. Turning to FIG. 5A, an illustrative environment 500A is shown with the original image 502, a synthetic speckled image 504, a denoised image 506, and feature maps 508A, 508B, 508C, 508D, 508E, 508F, 508G, and 508H. In FIG. 5B and the continued illustrative environment 500B, the remaining features maps 508I, 508J, 508K, 508L, 508M, 508N, 508O, and 508P are depicted. In some embodiments, the speckle removal system 124 generates the denoised image 506 using the trained machine learning model 158, such as the trained convolutional autoencoder 118, and the synthetic speckled image 504. The feature maps 508A, 508B, 508C, 508D, 508E, 508F, 508G, 508H, 508I, 508J, 508K, 508L, 508M, 508N, 508O, and 508P can be generated at a layer of the trained machine learning model 158, such as the trained convolutional autoencoder 118. The sixteen feature maps 508A, 508B, 508C, 508D, 508E, 508F, 508G, 508H, 508I, 508J, 508K, 508L, 508M, 508N, 508O, and 508P (which each can be 64×95) could correspond to the output from the convolutional layer 404F, with sixteen channels, of the convolutional autoencoder 400 of FIG. 4A. The output of the machine learning model is the denoised image 506, which can be based on the intermediate output from the feature maps 508A, 508B, 508C, 508D, 508E, 508F, 508G, 508H, 508I, 508J, 508K, 508L, 508M, 508N, 508O, and 508P and other intermediate output, as described herein.

Figure 6A:
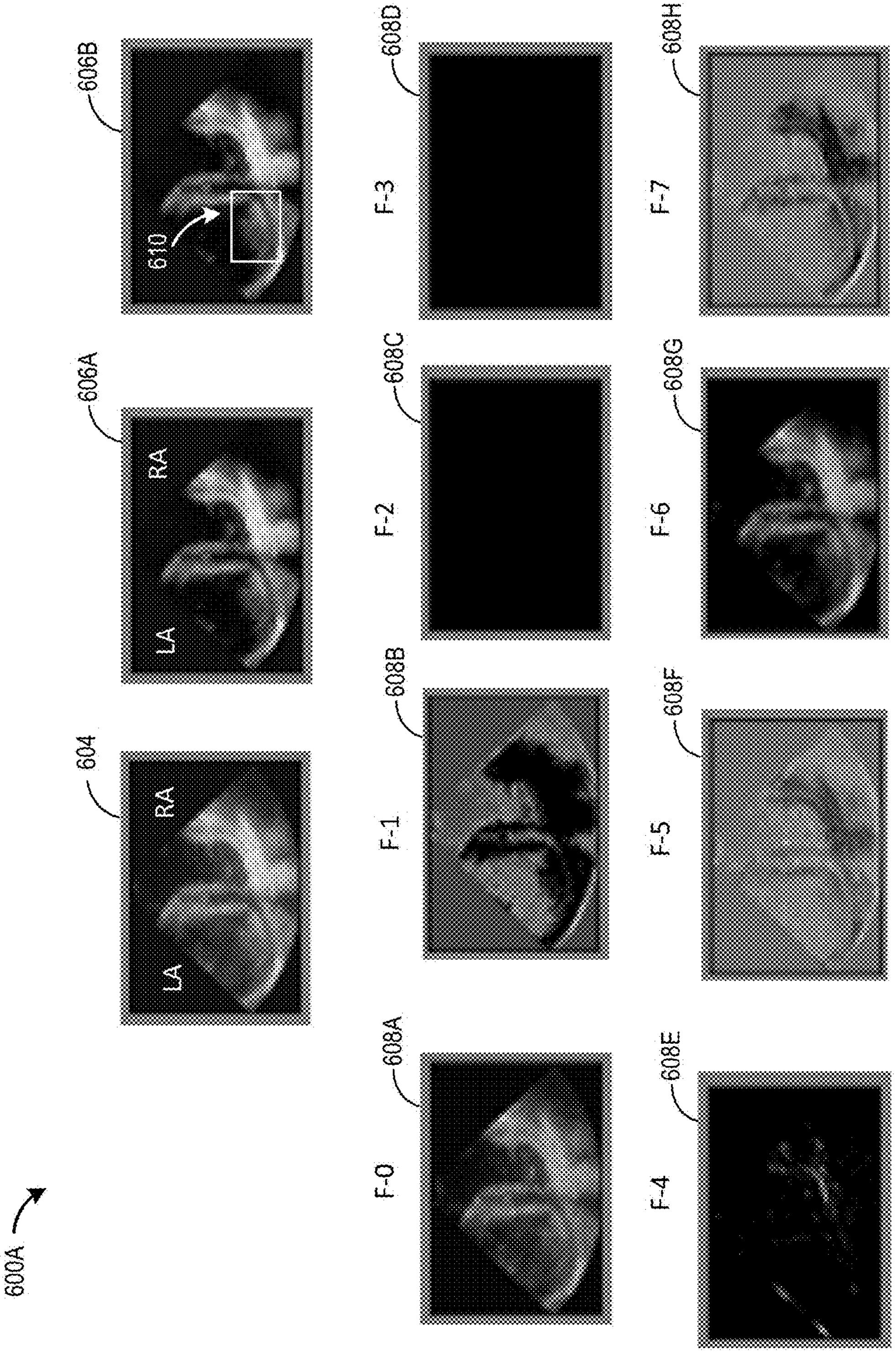
FIGS. 6A and 6B depict examples of a speckled image, a denoised image, and the feature maps of a trained machine learning model, such as a convolutional autoencoder, during image generation.
Figure 6B:
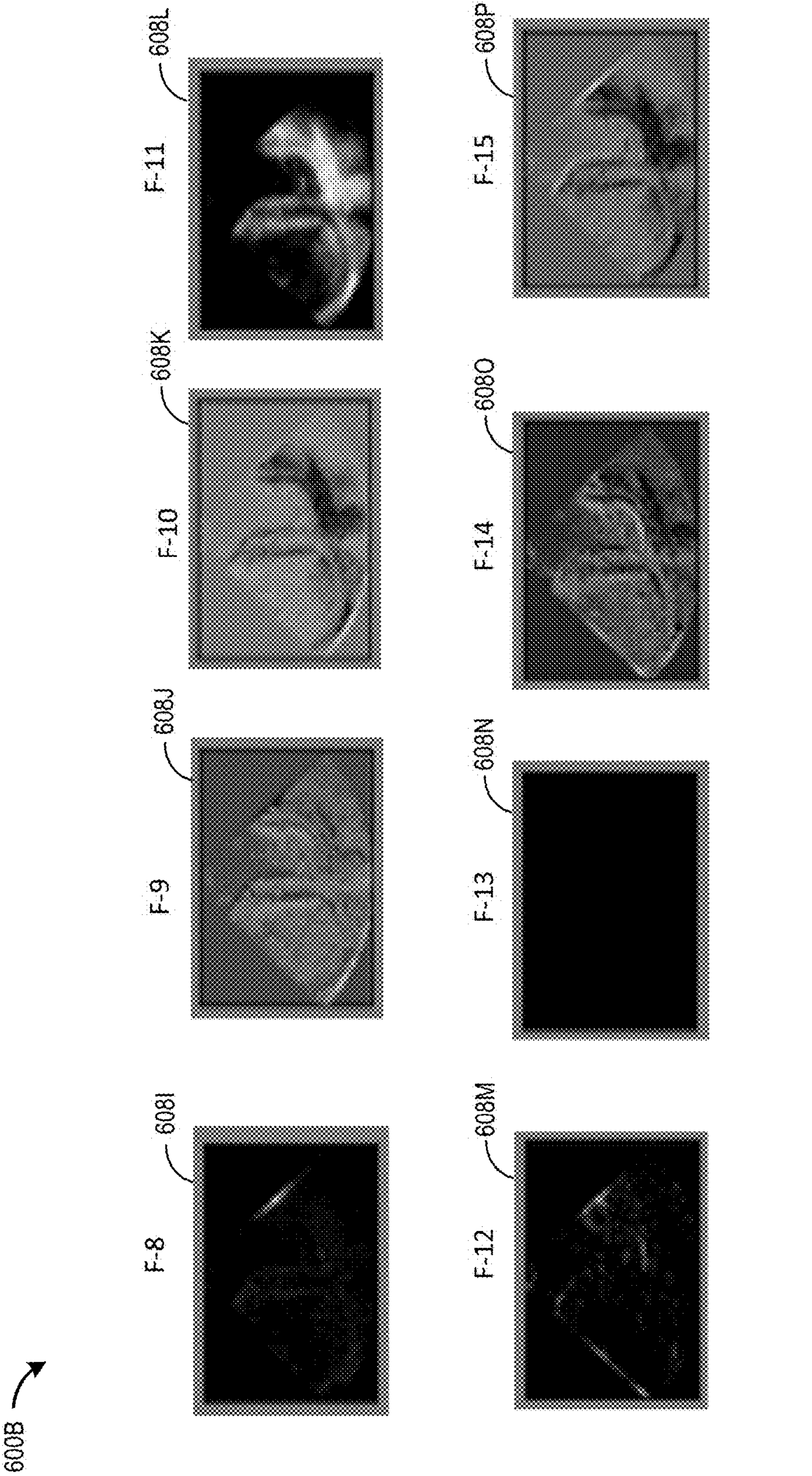

FIGS. 6A and 6B depict examples of a speckled image, a denoised image, and the feature maps during image generation. Turning to FIG. 6A, an illustrative environment 600A is shown with a speckled image 604 (with annotations), a denoised image 606A (with annotations), and feature maps 608A, 608B, 608C, 608D, 608E, 608F, 608G, and 608H. In FIG. 6B and the continued illustrative environment 600B, the remaining features maps 608I, 608J, 608K, 608L, 608M, 608N, 608O, and 608P are depicted. In some embodiments, the speckle removal system 124 generates the denoised image 606A using the trained machine learning model 158, such as the trained convolutional autoencoder 118, and the speckled image 604. During runtime prediction, the feature maps 608A, 608B, 608C, 608D, 608E, 608F, 608G, 608H, 608I, 608J, 608K, 608L, 608M, 608N, 608O, and 608P are generated at a layer of the trained machine learning model 158, such as the trained convolutional autoencoder 118. The sixteen feature maps 608A, 608B, 608C, 608D, 608E, 608F, 608G, 608H, 608I, 608J, 608K, 608L, 608M, 608N, 608O, and 608P (which each can be 64×95) could correspond to the output from the convolutional layer 404F, with sixteen channels, of the convolutional autoencoder 400 of FIG. 4A. The output of the trained machine learning model 158 is the denoised image 606A using the intermediate output from the feature maps 608A, 608B, 608C, 608D, 608E, 608F, 608G, 608H, 608I, 608J, 608K, 608L, 608M, 608N, 608O, and 608P and other intermediate output, as described herein.

The speckled image 604 can be an ICE image of an animal heart. The annotations in the speckled image 604 and the denoised image 606A and 606B have been added for illustrative and explanatory purposes and, in some embodiments, are neither input nor output of the model. As shown, the speckled image 604, with annotations, includes a left atrium (LA), a right atrium (RA), an interior atrial septum, and speckle throughout the image 604. The speckle removal system 124 advantageously generates the denoised image 606A and 606B with speckle removed. In particular, via the trained machine learning model 158, the speckle removal system 124 removes speckle from the left atrium, right atrium, and preserves the definition of the interior atrial septum between the left atrium and the right atrium in the denoised image 606A. Moreover, the speckle removal system 124 also preserves the feature 610 in the denoised image 606B and correctly does not remove it as speckle.

Figure 7A:
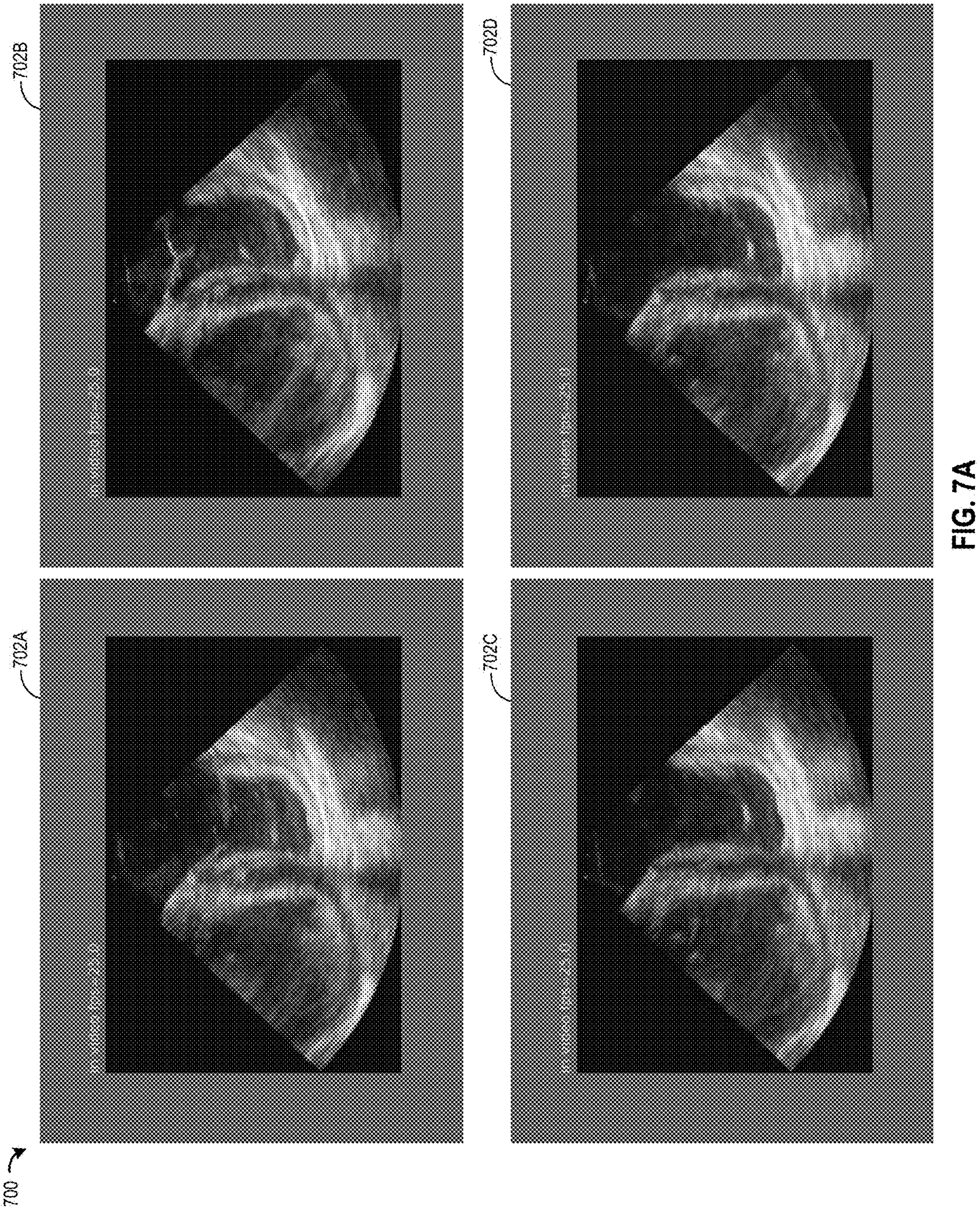
FIG. 7A depict example frames of an ultrasound video with speckle.
Figure 7B:
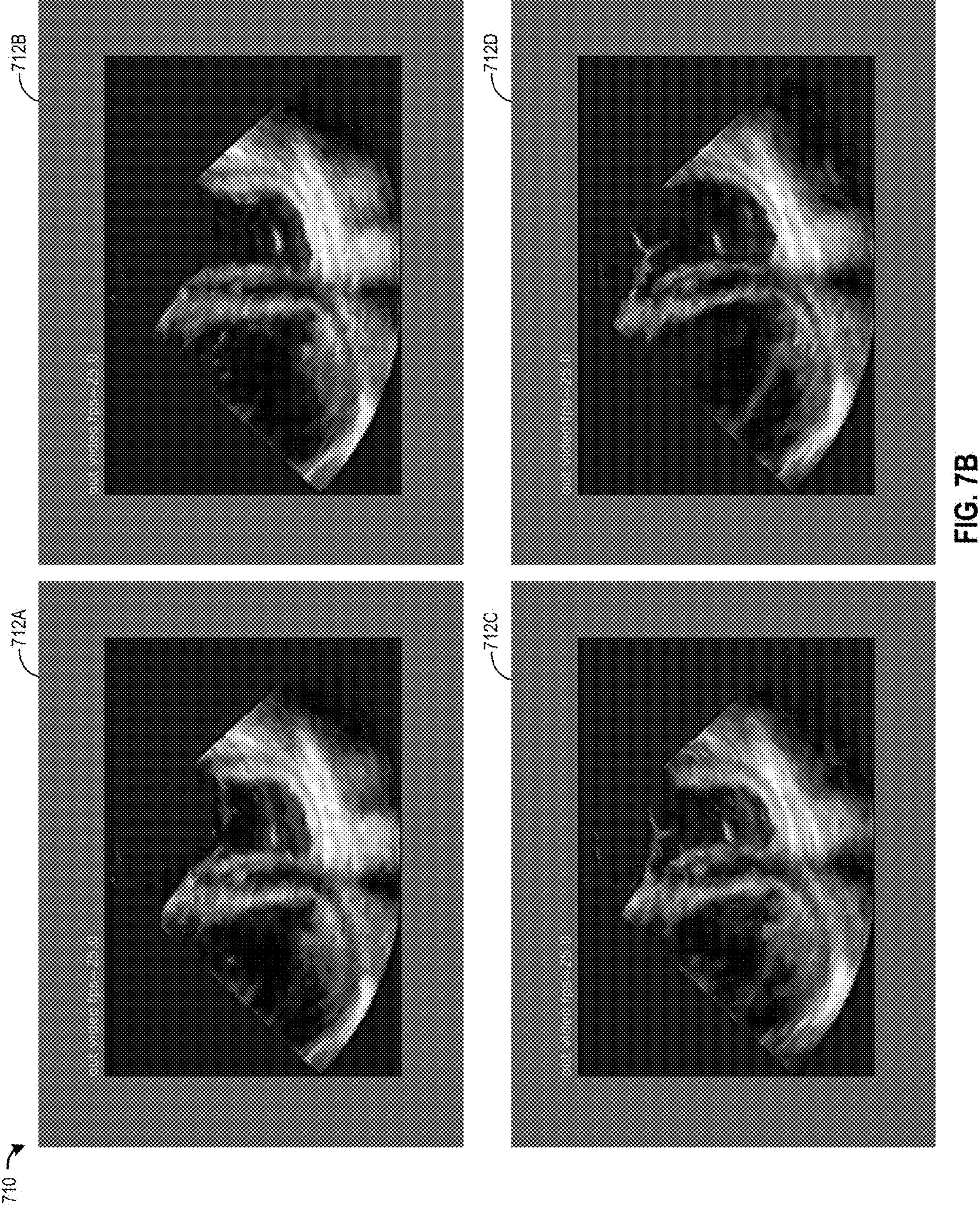
FIG. 7B depict example denoised frames of the ultrasound video.

FIG. 7A depict example frames of an ultrasound video with speckle. As shown, the set of frames 700 of an ultrasound video includes multiple frames 702A, 702B, 702C, and 702D. Also as shown, each of the multiple frames 702A, 702B, 702C, and 702D include speckle. The set of frames 700 can be from an ultrasound video taken during live ultrasound imaging. As described herein, the speckle removal system 124 can receive each frame from the set of frames 700 as captured substantially in real-time. The speckle removal system 124 can denoise each frame from the set of frames 700. FIG. 7B depicts example denoised frames of the ultrasound video. The speckle removal system 124 can output the set of denoised frames 710 of the ultrasound video. As shown, the set of denoised frames 710 includes multiple frames 712A, 712B, 712C, and 712D. Also, as shown, the speckle removal system 124 removed speckle from each of the multiple frames 712A, 712B, 712C, and 712D.

As shown by the set of denoised frames 710, the speckle removal system 124 removes speckle from the left atrium, right atrium, and preserves the definition of the interior atrial septum in the denoised image. Moreover, the speckle removal system 124 advantageously keeps the valves, which can be seen opening and closing, in the denoised frames 710, such as depicted in the third and fourth frames 712C and 712D.

As described herein, the set of denoised frames 710 can be presented as a video during live ultrasound imaging, such as during substantially in real-time interventional cardiology. A clinician can use a user interface to activate (or deactivate) the substantially in real-time automatic speckle removal, which can be helpful for a clinician during a procedure, such as repairing or installing a device in the heart.

Figure 8:
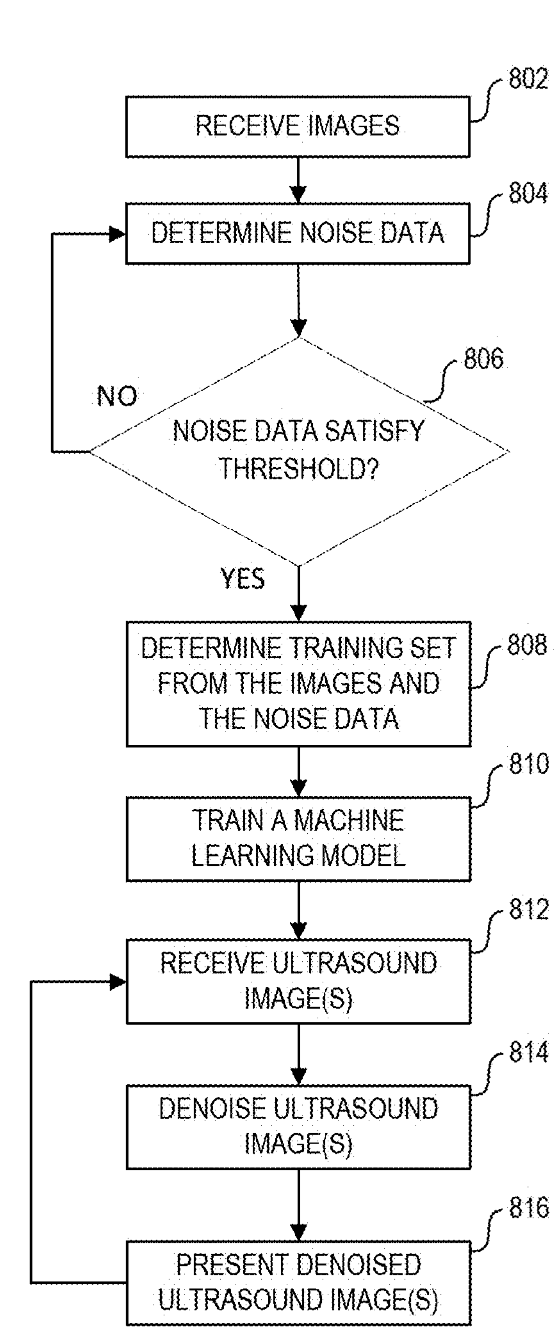
FIG. 8 is a flow chart depicting a method for creating a training set, training a machine learning model, and using the trained machine learning model for speckle removal.

FIG. 8 is a flow chart depicting a method 800 for creating a training set, training a machine learning model, and using the trained machine learning model for speckle removal. Advantages of the method 800 can include creating synthetic training data, which can avoid the training data creation problem of existing methods. Advantages of the method 800 can also include training a machine learning model that can remove speckle from images with fewer computing resources than existing mathematical-formula/image-filter based approaches.

Beginning at block 802, images can be received. The speckle removal system 124 can receive images, such as MRI images 102 or X-ray images. A data analyst can collect a set of digital tissue images. Advantages of the speckle removal system 124 is that the images can be non-cardiac images. For example, the images could be of the brain. In other cases, the images can be intracardiac images. The initial images (such as a set of digital tissue images) can be collected. In some cases, a data analyst can collect the initial images to be used for training.

At block 804, noise data can be determined. The speckle removal system 124 can create noise data. The speckle removal system 124 can determine the noise data from a Rayleigh distribution. In particular, the speckle removal system 124 can utilize a random number generator, such as a Rayleigh noise generator function, to determine initial noise data. The speckle removal system 124 can modify the noise data with at least a filter that results in speckle filter data. The speckle removal system 124 can apply a filter to the noise data that results in speckle filter data. As described herein, the filter can be a median filter or a mean filter. The speckle removal system 124 can utilize a filter to process each pixel in the image. In particular, for each pixel, the filter looks at its nearby neighbor pixels and replaces the pixel value with the mean or median of the neighboring pixel values. As used herein, the surrounding neighborhood can be called a kernel. The speckle removal system 124 can use one or more kernel sizes, such as 7×7 or 15×15. In some embodiments, the speckle removal system 124 can sectorize the noise data. The synthetic sector noise data can advantageously simulate the physical phenomenon of speckle that appears in ultrasound images. In some cases, in the sector noise data, as the shape widens (for example, see the sector noise data 206A of FIG. 2 in the direction of the value "250" on the Y axis), the speckle gets more stretched out in the horizontal direction.

In some embodiments, the speckle removal system 124 can use multiple sector options based on specified (such as user-specified) speckle size parameters. The speckle removal system 124 can receive a speckle size parameter. The speckle removal system 124 can modify the noise data by applying a sector geometric transformation and selecting a kernel size using the speckle size parameter that results in the speckle filter data. The speckle size parameter can include at least one of a beam spread or a speckle size growth parameter as a function of depth. As described herein, a user, such as an ultrasound physicist, can input a speckle size parameter that defines axial and lateral speckle extension per unit of distance (such as centimeter) and per scan line, together with sector angle and depth metadata. The speckle removal system 124 can perform geometric transformations on a sector-form speckle field so that lateral speckle elongation increases with depth according to a provided function, while maintaining the sector geometry and the correspondence between the rectangular source image and the sectorized result. To reduce overfitting to a particular frequency or probe setup, the speckle removal system 124 can train on multiple training datasets spanning different user-defined parameters and sector angles, allowing the machine learning model 140 to learn despeckling that can be robust across varied operating conditions.

In some embodiments, the speckle removal system 124 can apply a weighted summation to the noise data. The speckle removal system 124 can modify the noise data by applying a weighted summation to the noise data and filtered data that results in the speckle filter data. For example, the speckle removal system 124 can overlay sector-converted speckle with additional Rayleigh-distribution noise components in a selectable manner, thereby generating more versatile and realistic synthetic speckle and enabling control over which visual artifacts are suppressed. The speckle removal system 124 can determine a weighted sum where sectorized speckle is combined with Rayleigh noise and a filtered Rayleigh component prior to adding the result, scaled by a factor, to a sectorized source image. An example weighted sum could be 0.80×sectorized speckle+0.15×Rayleigh noise+0.05×filtered Rayleigh component, scaled by a factor and then summed with the original image. In some cases, the weight sum combination can capture dot-like or cloud-like scatterer characteristics of an ultrasound, including blood flow and sub-wavelength reflectors that may not present as classic speckle, and the Rayleigh components can themselves be sectorized by applying a sector stencil before overlay. The relative weights and scaling can be adjustable to reflect the noise characteristics of a given modality. A weighted summation approach can accommodate source images from different sources, such as, but not limited to, MRI, computed tomography, or cleaner ultrasound modalities such as transesophageal echocardiography. The weighted summation approach can support ICE training that narrows the visual clarity gap while preserving anatomical fidelity in the synthetic data.

At block 806, it can be determined whether the noise data satisfies a threshold. For example, the speckle removal system 124 can determine a metric (such as distance between individual speckles in the noise data or a statistical measure of distance between speckles) and compare the metric to a threshold value. In some cases, there can be multiple threshold values depending on a location associated with the metric. For example, the threshold can be different for a speckle metric as the shape of the sector noise data widens. If a threshold is satisfied, then the method proceeds to block 808 to determine a training set. If the threshold is not satisfied, then the method returns to block 804 to determine noise data gain. For example, the speckle removal system 124 can change one or more variables for noise data creation, such as increasing or decreasing the kernel size, determining the additional noise data, and checking whether the additional noise data satisfies a threshold at block 806.

At block 808, a training set can be determined from the images and the noise data. The speckle removal system 124 can determine, from the set of initial training images (such as a set of tissue images), a set of synthetic speckled images. As described herein, the speckle removal system 124 can create noise data and determine speckle filter data from the noise data. The speckle removal system 124 can apply, to a training image from the set of initial training images, the speckle filter data as an overlay that results in a synthetic speckled image (such as a synthetic speckled tissue image). The synthetic speckled image can be an intermediate synthetic speckled image. The speckle removal system 124 can transform the intermediate synthetic speckled image into a synthetic speckled image in a sector format. The speckle removal system 124 can transform a synthetic speckled tissue image into a sectorized synthetic speckled tissue image. The speckle removal system 124 can edit the intermediate synthetic speckled image to have a shape comprising two straight edges and a curved edge. The speckle removal system 124 can edit the intermediate synthetic speckled image by modifying pixels in the intermediate synthetic speckled image without removing any features from the intermediate synthetic speckled image. In other embodiments, the speckle removal system 124 can edit the intermediate synthetic speckled image by cropping at least a portion of the first intermediate synthetic speckled image. Moreover, the speckle removal system 124 can determine, from the set of initial training images (such as a set of tissue images), a set of images as targets for training. The speckle removal system 124 can create a training set comprising (i) the set of synthetic speckled images and (ii) the set of images as targets.

At block 810, a machine learning model can be trained. The speckle removal system 124 can train a machine learning model, such as a generative model or a convolutional autoencoder with the training set. As described herein, the speckle removal system 124 trains the machine learning model (such as a convolutional autoencoder or a U-Net model) with the synthetic training data until a threshold is satisfied, such as loss being sufficiently low and/or stable, which results in the trained machine learning model. Based on differences between an original image and output of a denoised image, the speckle removal system 124 can train the machine learning model using backpropagation, where the gradient of the loss with respect to the weights is computed and used to update the weights of the machine learning model.

The speckle removal system 124 can train the machine learning model by applying a region-of-interest mask to the training set and implementing a transformer-type attention mechanism. The transformer-type attention mechanism can compute attention scores between feature locations. The attention in the transformer-type attention mechanism can be gated by the region-of-interest mask such that attention weights outside the masked region are attenuated during training while attention weights within the masked region are emphasized. The transformer-type attention mechanism can include multi-head self-attention or cross-attention between encoder and decoder features. The speckle removal system 124 can incorporate a transformer-style attention mechanism that allows each spatial location in an image to weight and aggregate information from other locations according to learned importance scores. The attention can operate as self-attention within a feature map or as cross-attention that relates decoder representations to encoder representations or to auxiliary guidance inputs, including user-specified regions of interest or anatomical priors. The attention mechanism can function in a fully data-driven mode or under partial guidance, thereby enhancing emphasis on clinically salient structures while preserving the system's ability to automatically identify informative regions.

At block 812, one or more ultrasound images can be received. The speckle removal system 124 can receive one or more ultrasound images. For example, the speckle removal system 124 can receive multiple ultrasound frames during an interventional cardiology procedure. The multiple ultrasound frames can be presented as a video. In some embodiments, a clinician can use a user interface to activate (or deactivate) substantially in real-time automatic speckle removal, which can be helpful for a clinician during a procedure.

At block 814, the one or more ultrasound images can be denoised. The speckle removal system 124 can, for each ultrasound frame from the multiple ultrasound frames, generate, via the machine learning model (such as a convolutional autoencoder), a denoised ultrasound frame. The machine learning model can receive an ultrasound image as input and can output a denoised ultrasound image. In the case of a convolutional autoencoder, in the encoder portion, the initial convolutional and pooling layers of the convolutional autoencoder can progressively reduce the spatial dimensions (width and height) of the input and intermediate feature maps. In the decoder portion of the convolutional autoencoder, reverses the encoding process by restoring the spatial dimensions of the feature maps while reducing the number of channels and/or features. The output of the convolutional autoencoder can be a denoised ultrasound image.

At block 816, the one or more denoised ultrasound images can be presented. The speckle removal system 124 can cause presentation, via a graphical user interface, of the denoised ultrasound image. For example, for each ultrasound frame from the multiple ultrasound frames, the speckle removal system 124 can cause presentation of the corresponding denoised ultrasound frame. The denoised ultrasound frames can be presented substantially in real-time during a procedure.

Figure 9:
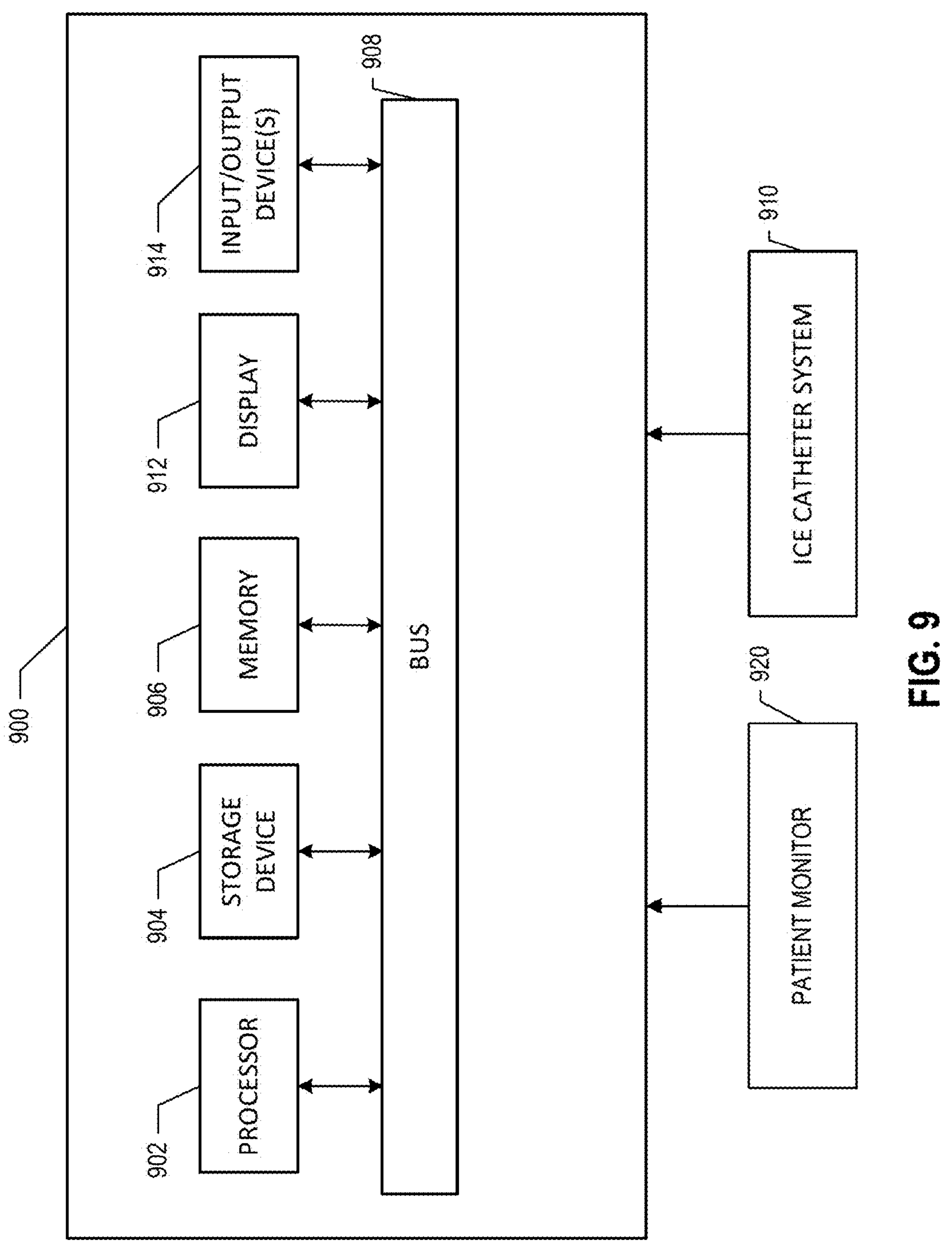
FIG. 9 is a block diagram illustrating an example computing system with which various methods and systems discussed herein may be implemented.

FIG. 9 is a block diagram that illustrates example components of a computing system 900. The computing system 900 can implement aspects of the present disclosure, such as the speckle removal system 124. The computing system 900 can receive data, such as ICE images, from an ICE catheter system 910. The computing system 900 can present images in the patient monitor 920. As described herein, the computing system 900 can, with a trained machine learning model 158, receive and denoise images.

The computing system 900 can include a hardware processor 902, a data storage device 904, a memory device 906, a bus 908, a display 912, and one or more input/output devices 914. The hardware processor 902 can also be implemented as a combination of computing devices, e.g., a combination of a digital signal processor and a microprocessor, a plurality of microprocessors, one or more microprocessors in conjunction with a digital signal processor, or any other such configuration. The hardware processor 902 can be configured, among other things, to execute instructions to perform one or more functions. The data storage device 904 can include a magnetic disk, optical disk, solid state drive, or flash drive, etc., and is provided and coupled to the bus 908 for storing information and computer-executable instructions. The data storage device 904 may be embodied in hard disk drives, solid state memories, or any other type of non-transitory computer readable storage medium. The memory device 906 can include one or more memory devices that store data, such as, without limitation, random access memory (RAM) and read-only memory (ROM). The computer-executable instructions can be loaded into the memory device 906. The computing system 900 may be coupled via the bus 908 to the display 912, such as an LCD display or touch screen, for displaying information to a user, such as a clinician. The patient monitor 920 can include a display, such as an LCD display or touch screen, and can similarly or alternatively display information to a user, such as a clinician. The computing system 900 may be coupled via the bus 908 to one or more input/output devices 914. The input device 914 can include, but is not limited to, a keyboard, mouse, digital pen, microphone, or touch screen.

It is to be understood that not necessarily all objects or advantages may be achieved in accordance with any particular embodiment described herein. Certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language used herein, such as, among others, "can," "might," "may," "e.g.," "for example," and the like, unless specifically stated otherwise, or otherwise understood within the context as used, is generally intended to convey that certain embodiments include, while other embodiments do not include, certain features, elements, or states. Thus, such conditional language is not generally intended to imply that features, elements or states are in any way required for one or more embodiments.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Such disjunctive language is not generally intended to, and should not, imply that certain embodiments require at least one of X, at least one of Y, and at least one of Z to each be present. Thus, the term "or" is used in its inclusive sense (and not in its exclusive sense) so that when used, for example, to connect a list of elements, the term "or" means one, some, or all of the elements in the list.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The terms "comprising," "including," "having," and the like are synonymous and are used inclusively, in an open-ended fashion, and do not exclude additional elements, features, acts, operations, and so forth.

The term "substantially" when used in conjunction with the term "real time" can refer to speeds in which no or little delay occurs. Substantially in real time can be associated with a threshold latency requirement that can depend on the specific implementation. In some embodiments, latency under 1 second, 500 milliseconds, 250 milliseconds, or 100 milliseconds can be substantially in real time depending on the specific context.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others.

What is claimed is:

1. A system comprising:

one or more non-transitory data storage media; and one or more first computer hardware processors in communication with the one or more non-transitory data storage media, wherein the one or more first computer hardware processors are configured to execute first computer-executable instructions to at least:

receive a set of tissue images;

determine, from the set of tissue images, a set of synthetic speckled tissue images, wherein to determine the set of synthetic speckled tissue images comprises:

create noise data;

modify the noise data with at least a filter that results in speckle filter data;

apply, to a first tissue image from the set of tissue images, the speckle filter data as an overlay that results in a first intermediate synthetic speckled tissue image; and transform the first intermediate synthetic speckled tissue image into a first synthetic speckled tissue image in a sector format, wherein the set of synthetic speckled tissue images comprises the first synthetic speckled tissue image;

determine, from the set of tissue images, a set of images as targets;

create a training set comprising (i) the set of synthetic speckled tissue images and (ii) the set of images as targets; and train a convolutional autoencoder with the training set.

2. The system of claim 1, further comprising:

one or more second computer hardware processors configured to execute second computer-executable instructions to at least:

receive a plurality of ultrasound frames during a cardiology procedure; and for each ultrasound frame from the plurality of ultrasound frames, generate, via the convolutional autoencoder, a denoised ultrasound frame, and cause presentation, via a graphical user interface, of the denoised ultrasound frame.

3. The system of claim 1, wherein the set of tissue images comprises non-cardiac images.

4. The system of claim 1, wherein to transform the first intermediate synthetic speckled tissue image into the first synthetic speckled tissue image in the sector format comprises:

edit the first intermediate synthetic speckled tissue image to have a shape comprising a first straight edge, a second straight edge, and a curved edge.

5. The system of claim 4, wherein to edit the first intermediate synthetic speckled tissue image to have the shape comprises:

modify pixels in the first intermediate synthetic speckled tissue image without removing any features from the first intermediate synthetic speckled tissue image.

6. The system of claim 4, wherein to edit the first intermediate synthetic speckled tissue image to have the shape comprises:

crop at least a portion of the first intermediate synthetic speckled tissue image.

7. A computer-implemented method comprising:

receiving a set of initial training images;

determining, from the set of initial training images, a set of synthetic speckled images, wherein determining the set of synthetic speckled images comprises:

creating noise data;

modifying the noise data with at least a filter that results in speckle filter data; and applying, to a first training image from the set of initial training images, the speckle filter data as an overlay that results in a first synthetic speckled image, wherein the set of synthetic speckled images is determined from the first synthetic speckled image;

determining, from the set of initial training images, a set of images as targets;

creating a training set comprising (i) the set of synthetic speckled images and (ii) the set of images as targets; and training a machine learning model with the training set.

8. The computer-implemented method of claim 7, training the machine learning model comprises:

applying a region-of-interest mask to the training set and implementing a transformer-type attention mechanism that computes attention scores between feature locations, wherein attention in the transformer-type attention mechanism is gated by the region-of-interest mask such a first attention weight outside a masked region is attenuated during training while a second attention weight within the masked region is emphasized, and wherein the transformer-type attention mechanism comprises multi-head self-attention or cross-attention between encoder and decoder features.

9. The computer-implemented method of claim 7, further comprising:

receiving a speckle size parameter, wherein modifying the noise data further comprises:

applying a sector geometric transformation and selecting a kernel size using the speckle size parameter that results in the speckle filter data.

10. The computer-implemented method of claim 9, wherein the speckle size parameter comprises at least one of a beam spread or a speckle size growth parameter as a function of depth.

11. The computer-implemented method of claim 7, wherein modifying the noise data further comprises:

applying a weighted summation to the noise data and filtered data that results in the speckle filter data.

12. The computer-implemented method of claim 7, wherein creating the noise data further comprises:

determining the noise data from a Rayleigh distribution.

13. The computer-implemented method of claim 7, wherein the filter comprises a median filter or a mean filter.

14. A system comprising:

one or more non-transitory data storage media; and one or more first computer hardware processors in communication with the one or more non-transitory data storage media, wherein the one or more first computer hardware processors are configured to execute first computer-executable instructions to at least:

receive a set of initial training images;

determine, from the set of initial training images, a set of synthetic speckled images, wherein to determine the set of synthetic speckled images comprises:

create noise data;

modify the noise data with at least a filter that results in speckle filter data; and apply, to a first training image from the set of initial training images, the speckle filter data as an overlay that results in a first synthetic speckled image, wherein the set of synthetic speckled images is determined from the first synthetic speckled image;

determine, from the set of initial training images, a set of images as targets;

create a training set comprising (i) the set of synthetic speckled images and (ii) the set of images as targets; and train a machine learning model with the training set.

15. The system of claim 14, further comprising:

one or more second computer hardware processors configured to execute second computer-executable instructions to at least:

receive an ultrasound image;

generate, via the machine learning model, a denoised ultrasound image; and cause presentation, via a graphical user interface, of the denoised ultrasound image.

16. The system of claim 14, wherein to determine the set of synthetic speckled images comprises:

transform the first synthetic speckled image into a sectorized synthetic speckled image, wherein the set of synthetic speckled images comprises the sectorized synthetic speckled image.

17. The system of claim 14, wherein the machine learning model corresponds to at least one of a convolutional autoencoder or a U-Net model.

18. The system of claim 14, further comprising:

one or more second computer hardware processors configured to execute second computer-executable instructions to at least:

receive a plurality of ultrasound frames during a cardiology procedure; and for each ultrasound frame from the plurality of ultrasound frames, generate, via the machine learning model, a denoised ultrasound frame, and cause presentation, via a graphical user interface, of the denoised ultrasound frame.

19. The system of claim 14, wherein to train the machine learning model comprises:

apply a region-of-interest mask to the training set and implement a transformer-type attention mechanism that computes attention scores between feature locations, wherein attention in the transformer-type attention mechanism is gated by the region-of-interest mask such a first attention weight outside a masked region is attenuated during training while a second attention weight within the masked region is emphasized, and wherein the transformer-type attention mechanism comprises multi-head self-attention or cross-attention between encoder and decoder features.

20. The system of claim 14, wherein to modify the noise data further comprises:

apply a weighted summation to the noise data and filtered data that results in the speckle filter data.

* * * * *